US006461876B1

(12) United States Patent
Giri

(10) Patent No.: US 6,461,876 B1
(45) Date of Patent: Oct. 8, 2002

(54) CHEMILUMINESCENT 1,2-DIOXETANES

(76) Inventor: Brij P. Giri, 36725 LaMarra, Sterling Heights, MI (US) 48310

( * ) Notice: Subject to any disclaimer, the term of this patent is extended or adjusted under 35 U.S.C. 154(b) by 69 days.

(21) Appl. No.: 09/643,063

(22) Filed: Aug. 21, 2000

Related U.S. Application Data

(60) Provisional application No. 60/099,693, filed on Sep. 8, 1998.

(51) Int. Cl.[7] .......................... G01N 33/533; C07F 9/06; C07D 321/00; C07C 43/166; C07C 43/168
(52) U.S. Cl. .................... 436/546; 530/391.3; 530/402; 530/406; 549/221; 556/446; 568/660
(58) Field of Search ................................. 549/221, 332; 568/660; 556/446; 530/391.3, 402, 406; 436/546

(56) References Cited

U.S. PATENT DOCUMENTS

| | | | |
|---|---|---|---|
| 5,004,565 A | 4/1991 | Schaap | |
| 5,112,960 A | 5/1992 | Bronstein et al. | |
| 5,225,584 A | 7/1993 | Brooks et al. | |
| 5,578,253 A | 11/1996 | Schaap et al. | |
| 5,679,803 A | 10/1997 | Bronstein et al. | |
| 5,721,370 A | 2/1998 | Akhavan-Tafti et al. | |

*Primary Examiner*—Mary E. Ceperley
(74) *Attorney, Agent, or Firm*—Plunkett & Cooney, PC; Arnold S. Weintraub

(57) ABSTRACT

The present invention provides novel 1,2-dioxetanes derived from spiro-fused ketones with or without π-electrons in the ring or with carbon-carbon double bond(s) in the spiro-fused ring. Additionally, these new dioxetanes have electron donating or withdrawing groups at the four-membered peroxide ring to render these dioxetanes active at all sites.

4 Claims, No Drawings

CHEMILUMINESCENT 1,2-DIOXETANES

CROSS REFERENCE TO RELATED APPLICATION

This application is a national application based on PCT Application, Serial No. 99/20590, filed Sep. 8, 1999, which is a completion application of U.S. provisional patent application Serial No. 6-0/099,693, filed Sep. 8, 1998 for "Chemiluminescent 1,2 dioxetanes", the disclosures of which are hereby incorporated by reference.

BACKGROUND OF THE INVENTION

1. Field of the Invention

The present invention relates to chemiluminescent compounds. More particularly, the present invention concerns stable, triggerable chemiluminescent 1,2-dioxetanes. Even more particularly, the present invention concerns new chemiluminescent 1,2-dioxetane compounds derived from the oxidation of novel alkenes prepared by the coupling of substituted aromatic esters or ketones and spiro-fused ketones with or without a T-electron system or a carbon-carbon double bond in the ring.

2. Prior Art

Chemiluminescent compounds, their preparation and their uses have been long documented in the prior art. These "high energy" molecules store sufficient energy to generate, or fragmentation, electronically excited carbonyl products which are responsible for the observed chemiluminescence. Dioxetanes and especially, 1,2-dioxitanes and eminently useful to detect the presence, as well as the absence, of certain enzymes in fluids such as blood and the like because of their chemiluminescence. Thus, 1,2 dioxetanes are eminently useful in doing medical assays.

Generally, 1,2-dioxetanes are thermally labile substances having a wide range of stability which decompose on heating and emit light, and correspond to the following formula (1):

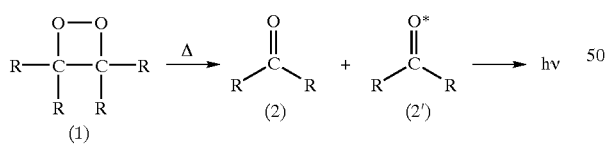

Where each R corresponds to any one of a multitude of organic moieties widely reported in the prior art, as detailed herebelow. As noted these 1,2-dioxetanes have a wide range of stability. For example, the prior art, as found in: (a) K. W. Lee, L. A. Singer and K. D. Legg, J.Org.Chem., 41, 2685 (1976); (b) F. McCapra, I. Beheshti, A. Burford, R. A. Hanu and K. A. Zaklika, J.Chem.Soc.,Chem.Commun., 944 (1977); and (c) J. H. Wieringa, J. Strating, H. Wynberg and W. Adam, Tet. Lett., 169 (1972); respectively, disclose the following 1,2-dioxetanes of different stability:

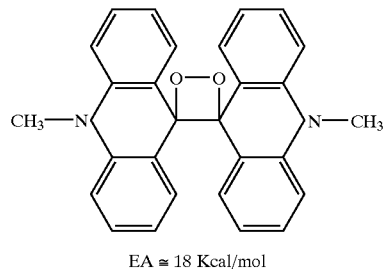

EA ≅ 18 Kcal/mol

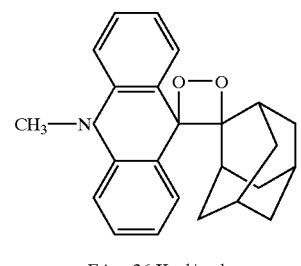

EA ≅ 26 Kcal/mol

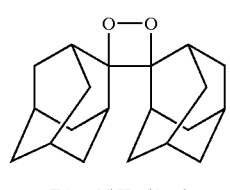

EA ≅ 35 Kcal/mol

Although these high energy compounds are all spiro-substituted 1,2-dioxetanes, spiroadamantane substitution exerts a tremendous stabilizing effect on these four-membered ring peroxides. The lower activation energy (EA) of the dioxetanes of formulae (3) and (4) above is explained by the donation of charge from nitrogen to the dioxetane ring. The dioxetane of formula (5) above decomposes at 150° C. and has a half life at 25° C. more than 20 years.

A 1,2-dioxetane (6) below, dispiro[adamantane2,3'-[1,2-]dioxetane-4',9'-fluorene] was isolated as crystals and described by W. Adam and L. A. A. Encarnacion, Chem. Ber., 115, 2592 (1982).

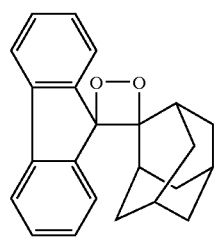

The stability of 1,2-dioxetanes (5) and (6) was described on the basis of bulky and rigid spiro nature of the adamantane group.

The first stable and enzymatic triggerable 1,2-dioxetane was synthesised by the oxidation of (6-acetoxy-2-naphthyl) methoxy methyleneadamantane as reported by A. P. Schaap, R. S. Handley and B. P. Giri, Tet. lett., 935 (1987). This 1,2-dioxetane utlizes aryl esterase emzyme to catalyze the cleavage of the acetate group of a naphthylacetate-substituted-1,2-dioxetane and produce chemiluminescence in aqueous buffers at ambient temperature by the following sequence:

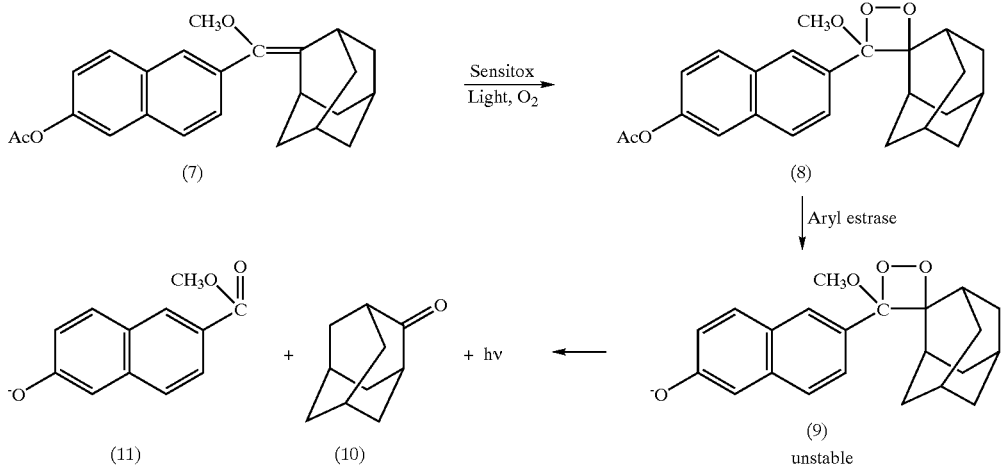

Several other stabilized 1,2-dioxetanes and their use as enzyme substrates have been disclosed in the literature. See, inter alia, A. P. Schaap, T. S. Chen, R. S. Handley, R. DeSilva and B. P. Giri, Tet. Lett., 1155(1987); A. P. Schaap, M. D. Sandison and R. S. Handley, Tet. Lett., 1159 (1987); U.S. Pat. Nos. 4,962,192; 4,978,614; 5,386,017; 5,721,370, the disclosures of which are hereby incorporated by reference.

These several other 1,2-dioxetanes, generally, have the following general structures:

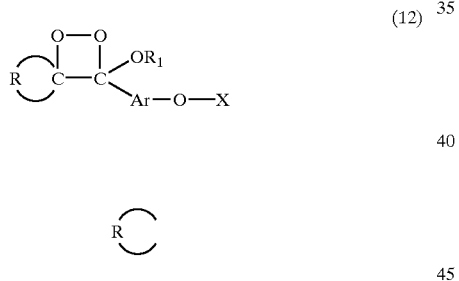

wherein

is a non-active site and which is selected from the group of polycyclic alkyl groups containing 6 to 30 carbon atoms, OX is an oxy group substituted on an aryl ring which forms an unstable oxide intermediate 1,2-dioxetane compound when triggered to remove X by an activating agent selected from the group consisting of an acid, a base, a salt, an enzyme and an inorganic or organic catalyst, and electron donor source, and X is a chemically labile group which is removed by the activating agents to form light and carbonyl containing compounds, $R_1$ is a lower alkyl containing 1 to 8 carbon atoms, or mixtures thereof, or (13)

$$\overset{O-O}{\underset{T}{C}-\underset{Y-Z}{C}}\overset{X}{\underset{}{}}$$

where T is a non-active site which is a cycloalkyl or a polycycloalkyl group bonded to the 4-membered ring portion of the dioxetane by a spiro linkage; Y is a fluorescent chromophore; X is a hydrogen, alkyl, aryl arylkyl, alkaryl, heteroalkyl, heteroaryl, cycloalkyl, cycloheteroalkyl, or enzyme cleavable group; and Z is hydrogen or an enzyme cleavable group, provided that at least one of X or Z must be an enzyme cleavable group.

The enzyme cleavable 1,2-dioxetanes of formulae (14), (15) and (16) shown below have been commercialized and used in immuno assays, southern blotting, northern blotting, western blotting, plaque/colony lifts and DNA sequencing.

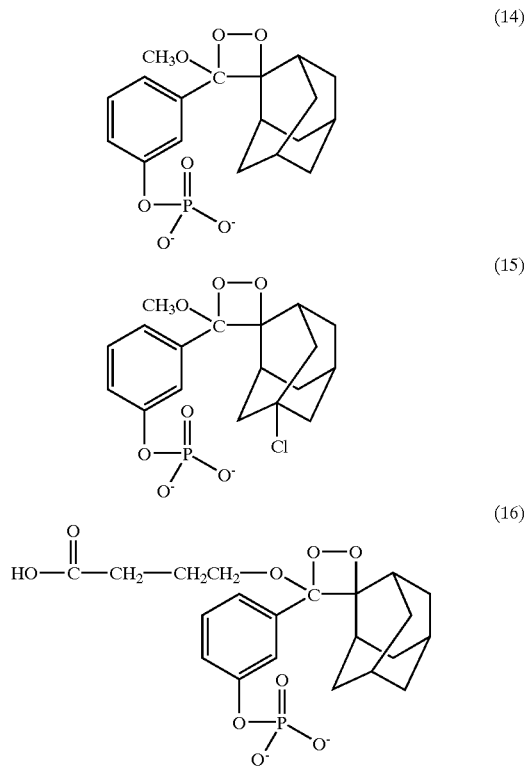

The 1,2-dioxetane of formula (15) with the chloro substitution in the adamantane ring demonstrates better results in DNA sequencing when compared to dioxetane (14). Dioxetane (16) is more soluble in an aqueous system than 1,2-dioxetane (14) and (15) when a $CH_3$ group is replaced with a $CH_2CH_2CH_2COOH$.

Other relevant prior art can be found in U.S. Pat. Nos. 5,386,017; 4,962,192; 5,018,827; 5,578,253; 5,004,565; 5,068,339, the disclosures of which are hereby incorporated by reference.

While these prior art compounds provide enzyme cleavable 1,2-dioxetanes, it has been observed that in an aqueous buffer, the luminescence of these molecules is particularity poor, especially when trace amounts of biological materials are sought to be detected. Thus more powerful dioxetanes are needed i.e. dioxetanes having higher levels of chemiluminescence in an aqueous buffer.

SUMMARY OF THE INVENTION

The present invention provides novel 1,2-dioxetanes derived from spiro-fused ketones with or without π-electrons in the ring or with carbon-carbon double bond(s) in the spiro-fused ring. Additionally, these new dioxetanes have electron donating or withdrawing groups at the four-membered peroxide ring to render these dioxetanes active at all sites.

The 1,2-dioxetanes hereof generally correspond to the formula:

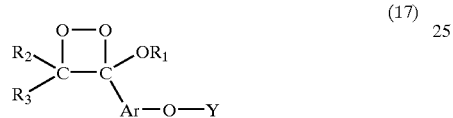  (17)

wherein (1) when Ar—O—Y and OR join together to give an aryl group substituted with an X-oxy group to form a stable 1,2-dioxetane intermediate which is triggerable to form an unstable intermediate oxide, $R_2$ and $R_3$ either form

  (a)

which is either a cyclic, polycyclic or spiro-fused ring containing at least one carbon-carbon double bond or carbon-carbon triple bond in the ring or side chain with or without heteroatoms or

  (b)

which is a cyclic, polycyclic or spiro-fused ring containing substituted or unsubstituted fused aromatic ring or substituted or unsubstituted aromatic ring attached by linker arms; or (2) when Ar—O—Y and OR, do not join together (a) Ar is aryl and may be phenyl, substituted phenyl, naphthyl, substituted naphthyl, anthryl, substituted anthryl or other aromatic or nonaromatic fluorescent or nonfluorescent group; Y is a hydrogen, alkyl, acetate, t-butyldimethylsilyl or an enzyme cleaveable group, an antibody cleaveable group; $R_1$ is selected from the group consisting of alkyl, aryl, aralkyl, alkaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, halogenated alkyl(mono, di, tri or any position in normal or branched or cyclic chain), alkylalcohol, alkylnitrile, alkylamine, alkylacid (mono or dibasic) or the inorganic salts thereof, haloalkylalcohol, haloalkylnitrile, haloalkylamine, haloalkylacid (mono or dibasic) or inorganic salts, linker-flourescent molecule, linker-antibodies, linker-antigen, linker-biotin, linker-avidin, linker-protein or linker-carbohydrates or linker-lipids; when $R_2$ and $R_3$ forms either

  (i)

which is a cyclic, polycyclic or spiro-fused ring containing at least one carbon-carbon double bond or cabon-carbon triple bond in the ring or side chain with or without heteroatoms, or

  (ii)

which is a cyclic, polycyclic or spiro-fused ring containing substituted or unsubstituted fused aromatic ring or substituted or unsubstituted aromatic rings attached by linker arms, or (b). Ar is aryl and may be phenyl, substituted phenyl, naphthyl, substituted naphthyl, anthryl, substituted anthryl or other aromatic or nonaromatic fluorescent or nonfluorescent group; Y is a hydrogen, alkyl, acetate, t-butyldimethylsilyl or an enzyme cleaveable group, or an antibody cleaveable group; $R_1$ is selected from the group consisting of alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, halogenated alkyl(mono, di, tri or any position in normal or branched or cyclic chain), alkylalcohol, alkylnitrile, alkylamine, alkylacid (mono or dibasic ) or the inorganic salts thereof, haloalkylalcohol, haloalkylnitrile, haloalkylamine, haloalkylacid (mono or dibasic) or inorganic salts, linker-flourescent molecule, linker-antibodies, linker-antigen, linker-biotin, linker-avidin, linker-protein or linker-or linker-lipids; when $R_2$ and $R_3$ form

, which is a cyclic or polycyclic alkyl group or spiro-fused ring with or without substitution or (c). Ar is aryl and may be phenyl, substituted phenyl, naphthyl, substituted naphthyl, anthryl, substituted anthryl or any other aromatic or nonaromatic fluorescent or nonfluorescent group; Y is a hydrogen, alkyl, acetate, t-butyldimethylsilyl or an enzyme cleaveable group, or an antibody cleaveable group; $R_1$ is selected from the group consisting of alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, halogenatedalkyl(mono, di, tri or any position in normal or branched or cyclic chain), alkylalcohol, alkylnitrile, alkylamine, alkylacid (mono or dibasic ) or the inorganic salts thereof, haloalkylalcohol, haloalkylnitrile, haloalkylamine, haloalkylacid (mono or dibasic) or inorganic salts, linker-flourescent molecule, linker-antibodies, linker-antigen, linker-biotin, linker-avidin, linker-protein or linker-carbohydrates or linker-lipids; where $R_2$ and $R_3$ are branched alkyl and cycloalkyl groups containing 3 to 8 carbon atoms which can contain halogens and hetero atoms in the ring or side chain thereof.

The new dioxetanes are triggered by the same activating agents described above.

The new alkenes hereof used to prepare the 1,2-dioxetanes hereof are prepared by the reaction of (a) 2-adamantanone or other spiro-fused ketone including ketones having a π-electron in the ring with (b) a substituted aromatic ester or ketone, using titanium trichloride or tetrachloride and a reducing agent such as an active metal or lithium aluminium hydride in tetrahydrofuran (THF) or other solvent of choice. This reaction is an intermolecular coupling of a ketone and an ester or ketone to form a vinyl ether using a modified McMurray procedure. Ordinarily, the reactants are present in at least stoichiometric quantities. However, excess amounts of the ester or ketone can be used. The temperatures at which the reactions as described above are those disclosed in the art.

Photooxygenation of the resulting vinyl ether by well-known conventional techniques affords 1,2-dioxetanes that are easily handled compounds with the desired stability.

The chemiluminescent decomposition of the 1,2-dioxetanes hereof, as noted above, can, preferably, can be conveniently triggered at room temperature by removing the protecting group with a fluoride ion, base or an enzyme to generate the unstable, aryloxide 1,2-dioxetane intermediate which cleaves to the starting materials and yields intense blue or other colored luminescence light.

For a more complete understanding of the present invention reference is made to the following detailed description and accompanying examples.

DESCRIPTION OF THE PREFERRED EMBODIMENTS

As stated above chemiluminescent enzyme substrates based on 1,2-dioxetane are well known in the literature for biological assays such as immunoassays and DNA probes. Use of these high energy compounds in biological systems requires 1,2-dioxetanes which are thermally stable at the temperature of the enzymatic reaction and which do not undergo rapid spontaneous decomposition in an aqueous buffer. The spiro-fused adamantyl dioxetanes hereof meet these requirements. The present 1,2-dioxetanes can be modified as substrates for various enzymes including aryl esterase, β-galactosidase, alkaline phosphatase and others.

In accordance herewith and as noted above, the present invention provides new 1,2-dioxetanes.These new 1,2-dioxetanes hereof correspond to the formula:

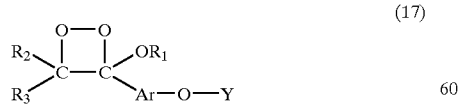

(17)

wherein
(1) when Ar—O—Y and OR join together to give an aryl group substituted with an X-oxy group to form a stable 1,2-dioxetane intermediate which is triggerable to form an unstable intermediate oxide, $R_2$ and $R_3$ either form

(a)

which is a cyclic, polycyclic or spiro-fused ring containing at least one carbon-carbon double bond or cabon-carbon triple bond in the ring or side chain with or without heteroatoms or

(b)

which is a cyclic, polycyclic or spiro-fused ring containing substituted or unsubstituted fused aromatic ring or substituted or unsubstituted aromatic ring attached by linker arms; or (2) when Ar—O—Y and $OR_1$ do not join together
  (a) Ar is aryl and may be phenyl, substituted phenyl, naphthyl, substituted naphthyl, anthryl, substituted anthryl or other aromatic or nonaromatic fluorescent or nonfluorescent group; Y is a hydrogen, alkyl, acetate, t-butyldimethylsilyl or an enzyme cleaveable group, or an antibody cleaveable group; $R_1$ is selected from the group consisting of alkyl, aryl, aralkyl, alkaryl, heteroalkyl, heteroaryl, cycloalkyl, cycloheteroalkyl, alkyletheralkyl, alkyletheraryl, alkyl(etheralkyl)$_2$, alkyl (etheralkyl)$_3$, alkyletherhaloalkyl, alkyl (etherhaloalkyl)$_2$, alkylalkene, alkylalkyne, arylalkene, arylalkyne, halogenated alkyl(mono, di, tri or any position in normal or branched or cyclic chain), alkylalcohol, alkylnitrile, alkylamine, alkylacid (mono or dibasic ) or the inorganic salts thereof, haloalkylalcohol, haloalkylnitrile, haloalkylamine, haloalkylacid (mono or dibasic) or inorganic salts, linker-flourescent molecule, linker-antibodies, linker-antigen, linker-biotin, linker-avidin, linker-protein or linker-carbohydrates or linker-lipids; when $R_2$ and $R_3$ form either

(i)

which is a cyclic, polycyclic or spiro-fused ring containing at least one carbon-carbon double bond or cabon-carbon triple bond in the ring or side chain with or without heteroatoms, or (ii)

(ii)

which is a cyclic, polycyclic or spiro-fused ring containing substituted or unsubstituted fused aromatic ring or substituted or unsubstituted aromatic ring attached by linker arms, or (b). Ar is aryl and may be phenyl, substituted phenyl, naphthyl, substituted naphthyl, anthryl, substituted anthryl or any other aromatic or nonaromatic fluorescent or nonfluorescent group; Y is a hydrogen, alkyl, acetate, t-butyldimethylsilyl or an enzyme cleaveable group, or an antibody cleaveable group; $R_1$ is selected from the group consisting of alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, halogenated alkyl(mono, di, tri or any position in normal or branched or cyclic chain), alkylalcohol, alkylnitrile, alkylamine, alkylacid (mono or dibasic) or the inorganic salts thereof, haloalkylalcohol, haloalkylnitrile, haloalkylamine, haloalkylacid (mono or dibasic) or inorganic salts, linker-flourescent molecule, linker-antibodies, linker-antigen, linker-biotin, linker-avidin, linker-protein or linker-carbohydrates or linker-lipids; when $R_2$ and $R_3$ form

which is a cyclic, polycyclic alkyl group with or without substitution which are spiro-fused to the dioxetane ring, or (c). Ar is aryl and may be phenyl, substituted phenyl, naphthyl, substituted naphthyl, anthryl, substituted anthryl or any other aromatic or nonaromatic fluorescent or nonfluorescent group; Y is a hydrogen, alkyl, acetate, t-butyldimethylsilyl or an enzyme cleaveable group, or an antibody cleaveable group; $R_1$ is selected from the group consisting of alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, halogenatedalkyl(mono, di, tri or any position in normal or branched or cyclic chain), alkylalcohol, alkylnitrile, alkylamine, alkylacid (mono or dibasic ) or the inorganic salts thereof, haloalkylalcohol, haloalkylnitrile, haloalkylamine, haloalkylacid (mono or dibasic) or inorganic salts, linker-flourescent molecule, linker-antibodies, linker-antigen, linker-biotin, linker-avidin, linker-protein or linker-simple or complex carbohydrates or linker-simple and complex lipids; where $R_2$ and $R_3$ are branched alkyl and cycloalkylgroups containing 3 to 8 carbon atoms which can contain halogens and hetero atoms in the ring or side chain thereof.

Typically, the new alkenes hereof are prepared by the reaction of (a) 2-adamantanone or other spiro-fused ketone including ketones having a π-electron in the ring with (b) a substituted aromatic ester or ketone, using titanium trichloride or tetrachloride and a reducing agent such as an active metal or lithium aluminium hydride in tetrahydrofuran (THF). This reaction is an intermolecular coupling of a ketone and an ester or ketone to form a vinyl ether using a modified McMurray procedure. Ordinarily, the reactants are present in at least stoichiometric quantities. However, excess amounts of the ester or ketone can be used. The temperatures at which the reactions as described above are those disclosed in the art.

Photooxygenation of the resulting vinyl ether affords 1,2-dioxetanes that are easily handled compounds with the desired stability.

When these dioxetanes react with an activating reagent or agent which removes the Y moiety (formula 17), they decompose to form an aryl oxide 1,2-dioxetane intermediate of the formula:

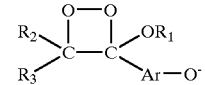 (18)

This aryl oxide oxides 1,2-dioxetane intermediate, then, spontaneously decomposes to produce light and compounds of the formulae:

 (19)

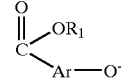 (20)

where compound (19) is the starting organic ketone and compound (20) is the residue of the starting organic ester or ketone when Ar O$^-$ and OR$_1$ join together.

In practicing the present invention, compound (19) can be any one of or a mixture of adamantan-2-one, substituted adamantan-2-one, adamantan-2-one-4,5-ene, substituted adamantan-2-one-4,5-ene, 2-hydroxytricyclo[7.3.1.0$^{2,7}$]tridecan-13-one or substituted 2-hydroxytricyclo[7.3.1.0$^{2,7}$]tridecan-13-one, tricyclo[7.3.1.0$^{2,7}$]tridec-2,7-ene -13-one or substituted tricyclo[7.3.1.0$^{2,7}$]tridec-2,7-ene-13-one, bicyclo[3.3.1]nonan-9-one or substituted bicyclo[3.3.1]nonan-9-one benzonorbonen-7-one or substitutrd benzonorbornen-7-one, 2,4-dimethyl-3-propanone or substituted 2,4-dimethyl-3-propanone, dicyclopropyl ketone or substituted dicyclopropyl ketone, dicyclohexyl ketone or substituted dicyclohexyl ketone when compound (20) is selected from the group consisting of substituted or unsubstituted 9H-fluoren-9-one, 9H-xanthen-9-one, 2,2,2-trifluoroethyl 3-hydroxybenzoate or substituted 2,2,2-trifluoroethyl 3-hydroxybenzoate, 2-phenoxyethyl 3-hydroxybenzoate or substituted 2-phenoxyethyl 3-hydroxybenzoate, and the like further the ketone of formula (19) is selected from the group consisting of adamantan-2-one-4,5-ene, substituted adamantan-2-one-4,5-ene, tricyclo[7.3.1.0$^{2,7}$]tridec-2,7-ene-13-one, substituted tricyclo[7.3.1.0$^{2,7}$]tridec-2,7-ene-13-one when the compound of formula (20) is alkyl or aryl 3-hydroxybenzoate or substituted alkyl or aryl 3-hydroxybenzoate.

The alkenes hereof used to prepare the present dioxetane correspond to the formula:

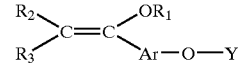 (21)

wherein $R_1$, $R_2$, $R_3$, Y and Ar are as described above,

These alkenes are prepared by the coupling of the above-described ketones and esters or ketones.

Generally, the intramolecular coupling reaction between the ketone and the ester or ketone is carried out at a temerature ranging from about 25° C. to about 85° C. and, perferably, from about 45° C. to about 65° C. A stocichiometric excess of either the ester or ketone may be used.

The coupling reaction is carried out in the presence of suitable solvents and active metals as described in the prior art denoted above, the disclosure above which are hereby incorporated by reference.

After the alkene is obtained it is then, photooxidized to form the stable, triggerable 1,2-dioxetane hereof. These dioxetanes can, then, be de-stablized or triggeredby the reaction with base, acid, enzyme and or inorganic or organic catalyst and or electron donor source in the presence or absence of a fluorscence compound, as described in the literature or above cited prior art.

For a more complete understanding of the present invention, reference is made to the following non-limiting examples. In the examples, all parts and percentages are by weight unless expressly stated to be otherwise.

In supporting the findings, the structures of the resulting compounds was confirmed by Nuclear Magnetic Resonance (NMR). NMR spectra were recorded on a General Electric QE 300 spectrometer in desired solvents using tetramethylsilane as an internal standard. Chemiluminescence kinetics were performed on a Monolight 1500 at room temperature. The purity of the materials were checked by TLC on silica gel plate. Melting points were measured in a MEL-TEMPII capillary melting point apparatus and are uncorrected. All the alkenes were dissolved in a suitable solvent and photooxidized by irradiation with 1000-W sodium lamp under bubbled oxygen at ice-water temperature in the presence of polystyrene-bound Rose Benzal as reported in the literature.

EXAMPLE I

This example illustrates the preparation of [(4-Methoxy)-4-(3-phosphoryloxyphenyl)]spiro[1,2-dioxetane-3,13'-(8-n-propyl)tricyclo[7.3.1,o$^{2,7}$]tridec-2,7-ene], disodium salt (32) in accordance with the present invention.The sequence of the reactions can be shown as:

(a) Synthesis of 8-n-propyl-2-hydroxytricyclo [7.3.1.0$^{2,7}$]tridecan-13-one (24)

Into a three-neck 500 mL round bottom flask equipped with magnetic stirrer and an oil bath under nitrogen was added 250 parts of cyclohexanone. The oil bath temperature was maintained at 70–75° C. with stirring. A solution of 2.5 parts of potassium hydroxide dissolved in 25 mL of absolute ethyl alcohol was added to the reaction flask in one portion. Thirty parts of butyraldehyde was dissolved in 35 mL of absolute ethyl alcohol and added dropwise to the reaction flask over a period of 6 hours. The reaction mixture was stirred at 70–75° C. for the 15 hours. After the reaction mixture was cooled to room temperature and refrigerated for 15 hours. The inside surface of the flask was scratched with a glass rod to precipitate out the white material and the flask was refrigerated for additional 4–5 hours. The white solid material was filtered and washed with 50 mL of cold water and then with 50 mL cold ether. The recovered solid was dried at room temperature and the yield was 35 parts. The solid showed a single spot on silica gel TLC plate eluted with 10% ethyl acetate/hexane. The structure of the material was confirmed on the basis of $^1$H NMR. This reaction proceded as follows:

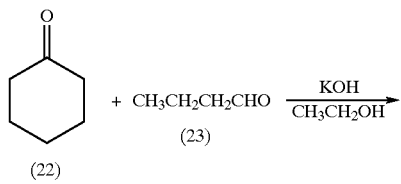

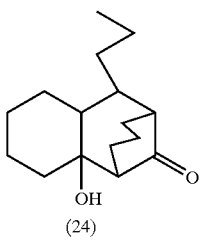

(b) Synthesis of 8-n-propyltricyclo[7.3.1.0$^{2,7}$]tridec-2,7-ene-13-one (25)

Into a round bottom flask equipped with heating mantle, magnetic stirrer and a water separator was charged with 150 parts of benzene, 5 parts of the hydroxy ketone (24) and 0.5 parts of concentrated sulfuric acid. The reaction mixture was heated under reflux for 12 hours. Water was separated and the TLC of the reaction mixture on silica gel plate showed two new spots and disappearance of the starting material. The reaction mixture was cooled to room temperature and the benzene solution was filtered. The solvent was removed under reduced pressure and the so-obtained oily material was dissolved in 150 mL of methylene chloride. The methylene chloride solution was washed twice with 50 mL of water and dried on anhydrous sodium sulfate. The solvent was removed under reduced pressure and the oily material was purified on silica gel column to give 3.18 parts of an oily nature compound. The structure of the material was confirmed on the basis of $^1$H NMR. The reaction proceded in accordance with the following equation:

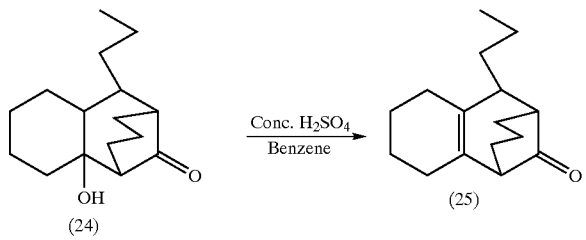

(c) Synthesis of Methyl 3-hydroxybenzoate (27)

Into a 2 L round bottom flask equipped with magnetic stirrer and heating mantle was added 100 parts of 3-hydroxy benzoic acid (26) 1.25 L of methanol and 2 mL of concentrated sulfuric acid. The reaction mixture was heated under gentle reflux for 12 hours. The solvent was evaporated under reduced pressure and the recovered solid material was dissolved in 500 mL of ethyl acetate. The organic layer was washed with 250 mL of water, 250 mL of 5% aqueous solution of sodium bicarbonate and 250 mL of water. The ethyl acetate layer was dried over anhydrous sodium sulfate and the solvent was evaporated under reduced pressure. The oily material was treated with n-hexane to give a solid material which when filtered under reduced pressure and dried at room temperature, yield 105 parts. TLC on silica gel plate showed a single spot. The structure of the compound was confirmed on the basis of $^1$H NMR. The material was prepared according to the following equation:

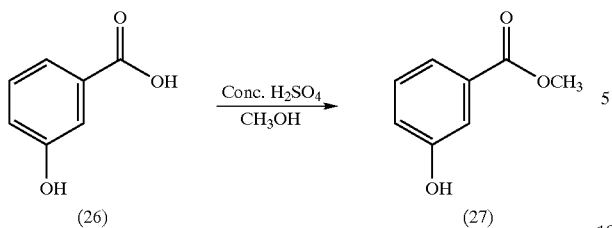

(d) Synthesis of Methyl 3-tert-butyldimethylsiloxybenzoate (28)

Into a 250 mL round bottom flask was added 50 mL of dry dimethyl formamide. Ffifteen parts of the hydroxy benzoate (27) and seventeen parts of tert-butyldimethyl silyl chloride were added to the reaction flask with stirring. Seventeen parts of Imidazole was added in portions and stirring was continued for 10 hours. The reaction mixture was extracted with (3×300 mL) of hexane and the hexane layer was washed twice with 250 mL of water. The organic layer was dried on anhydrous sodium sulfate and the solvent was evaporated under reduced pressure to give an oil, yield 26 parts. This material was pure enough for the next step of the reaction. The material was prepared according to the following equation:

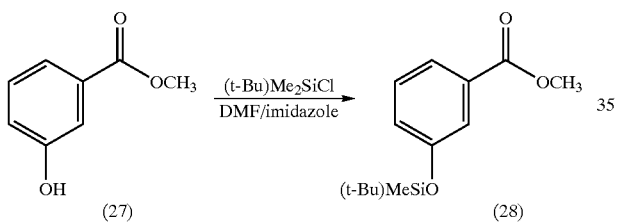

(e) Synthesis of (3-tert-butyldimethylsiloxyphenyl) methoxymethylene 8-n-propyltricyclo[7.3.1.0$^{2,7}$] tridec-2,7-ene (29)

Into a 500 mL three-neck flask equipped with magnetic stirrer, pressure-equalizing addition funnel and nitrogen line was charged with 200 mL anhydrous THF. Twelve parts of titanium tetrachloride was added dropwise over a period of 30 minutes. The suspension was stirred for 20 minutes and 17 parts of zinc was added in small portions. The reaction mixture was heated under reflux for 3 hours and 30 parts of triethylamine was added dropwise. After refluxing one hour a solution of 4 parts of ester (28) and 3 parts of ketone (25) in 50 mL of dry THF was added over a period of 90 minutes and the reaction mixture was heated for one hour. TLC on silica gel plate of the mixture shows the presence of the starting ester. Two and one half parts of ketone (25) in 20 mL of dry THF was added dropwise over 60 minutes and refluxed for two hours. The mixture was cooled to room temperature, diluted with 500 mL of hexane and decanated. The residue was washed with hexane (3×200 mL). The combined hexane layer was filtered and evaporated under reduced pressure to give an oily material which was purified by chromatography on silica gel column using 2.5% ethyl acetate/hexane as an eluant. The fractions were checked by TLC on silica gel plate and the desired fractions were combined. The solvent was evaporated under reduced pressure to give an oil, yield 5.2 parts. The structure was confirmed by $^1$H NMR. The reaction proceeded as follows:

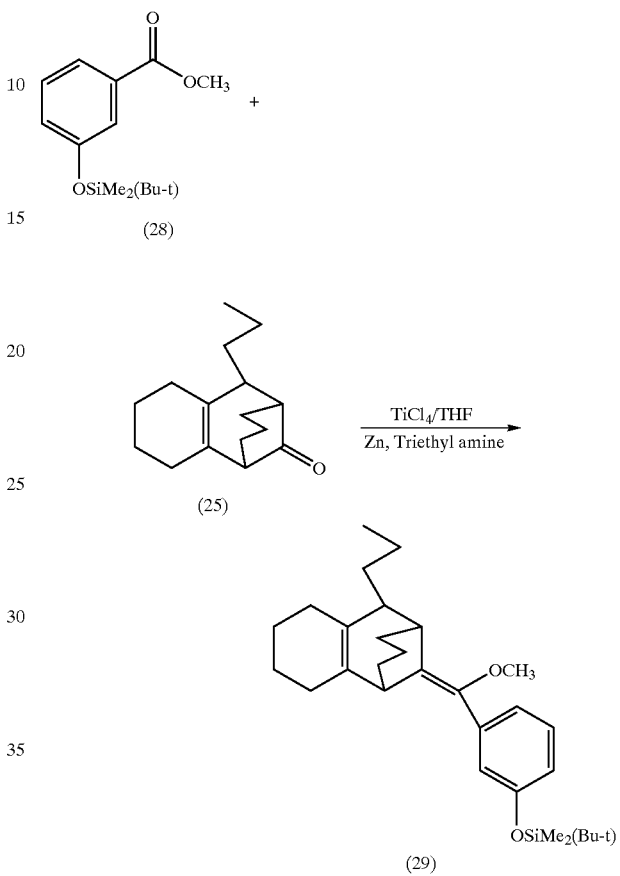

(f) Synthesis of (3-Hydroxyphenyl) methoxymethylene 8-n-propyltricyclo[7.3.1.0$^{2,7}$] tridec-2,7-ene (30)

To a solution of 5.2 parts of alkene (29) in 150 mL of THF was added to 7 parts of a (70%) tetra-n-butylammonium fluoride in 50 mL of THF over a period of 10 minutes and stirring was continued for the next two hours. TLC on silica gel plate showed the formation of new product. Solvent was evaporated under reduced pressure and the oily material was dissolved in 300 mL of methylene chloride and washed with 2×150 mL of water. After drying over anhydrous sodium sulfate, the solvent was evaporated and the oily product was purified on silica gel column. The fractions were checked by TLC on silica gel plate and the combined organic solvent was evaporated, yield 3.25 parts. The structure of the product was confirmed on the basis of $^1$H NMR. The reaction proceeded as follows:

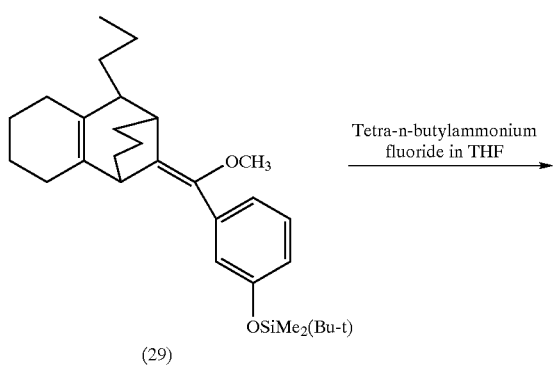

(29)

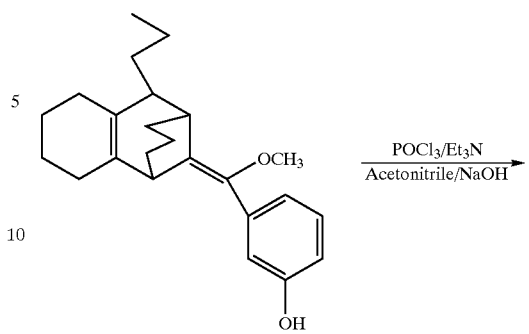

(30)

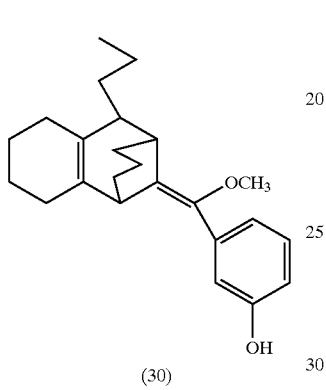

(30)

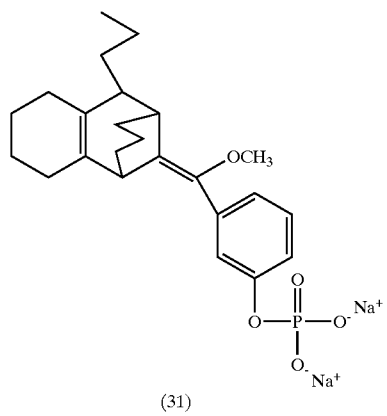

(31)

(g) Synthesis of (3-Phosphoryloxyphenyl) methoxymethylene 8-n-propyltricyclo[7.3.1.0$^{2,7}$] tridec-2,7-ene, Disodium Salt (31)

Into a 500 mL three-neck round bottom flask equipped with magnetic stirrer was added 60 mL of methylene chloride and 20 parts of triethyl amine under nitrogen at ice-water temperature. The reaction flask was cooled to ice-water temperature and 3.5 mL of phosphorous oxychloride was added to the reaction mixture over a period of 15 minutes. A solution of 3.5 parts of alkene (30) in 35 mL of methylene chloride was added dropwise over 30 minutes and was stirred for 2 hours. The solvent was evaporated under reduced pressure. The reaction mixture was extracted with 2×250 mL of hexanes containing 0.1% triethyl amine. Hexane was evaporated under reduced pressure and the product was dissolved in 50 mL of acetonitrile. A solution of 2.5 parts of sodium hydroxide in 25 mL of water was added dropwise and was stirred for two hours. Reaction mixture was diluted with 50 mL of acetonitrile and the solid was filtered. The solid was crystalized with methanol and acetone mixture. The solid was filtered, washed with acetone and dried, yield 2.9 parts. The reaction proceeded as follows:

(h) Photooxidation of (3-Phosphoryloxyphenyl) methoxymethylene 8-n-propyltricyclo[7.3.1.0$^{2,7}$] tridec-2,7-ene, Disodium Salt (31)

Alkene (31) was photooxidized by the above noted procedure, to give [(4-methoxy)-4-(3-phosphoryloxyphenyl)]spiro[1,2-dioxetane-3,13'-(8-n-propyl)tricyclo[7.3.1.0$^{2,7}$]tridec-2,7-ene]. disodium salt (32).

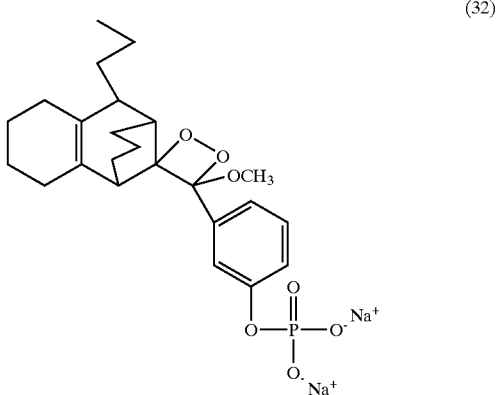

(32)

EXAMPLE II

This example illustrates the preparation of [(4-Methoxy)-4-(3-phosphoryloxyphenyl)]spiro[1,2-dioxetane-3,13- tricyclo[7.3.1,o$^{2,7}$]tridec-2,7-ene], disodium salt (39). This dioxetane was prepared by the sequence of the reactions in accordance herewith:

(a) Synthesis of 2-Hydroxytricyclo[7.3.1.0$^{2,7}$] tridecane-13-one (34)

Into a 500 mL three-neck round bottom flask equipped with magnetic stirrer and oil bath was added 250 parts of cyclohexanone (22) under nitrogen. The oil bath temperature was maintained at 80–85° C. with stirring. Sixty mL of absolute ethanol with 2.5 parts of potassium hydroxide was added in one portion. Sixteen parts of paraformaldehyde was added in small portions over a period of 3 hours and the temperature was maintained for 15 hours with stirring. The reaction mixture was cooled to room temperature and refrigerated at 40° C. for 15 hours. The inside surface of the flask and liquid was scratched with a glass rod. The solid started to separate and the flask was refrigerated for an additional 24 hours. The recovered solid was filtered under reduced pressure. The solid material was washed with 50 mL of water and two times with 50 mL of cold ether and dried, yield of 29 parts. The mother liquor was stored at −200° C. for 15 hours. The solid material was filtered and washed with water and ether, yield 10.0 parts. The combined solid was washed with hexane. The material showed a single spot on TLC on silica gel plate. The structure was confirmed on the basis of $^1$H NMR. The reaction proceeded as follows:

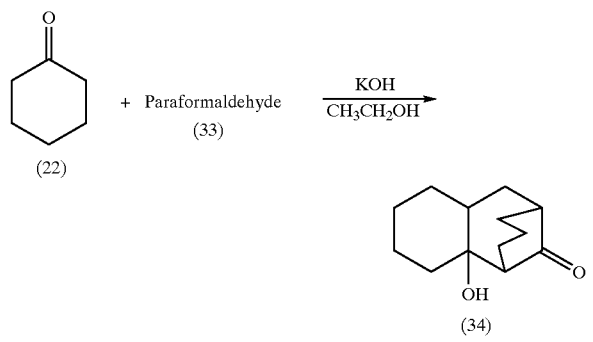

(b) Synthesis of Tricyclo[7.3.1.0$^{2,7}$]tridec-2,7-ene-13-one (35)

Into a 500 mL round bottom flask was added 5.0 parts of the hydroxy ketone (34). The product was dissolved in 150 mL of benzene by heating at 40° C. The reaction mixture was stirred at refluxing temperature for 12 hours in the presence of 0.5 parts of concentrated sulfuric acid. The reaction mixture was cooled to room temperature and the benzene solution was filtered. The solvent was evaporated under reduced pressure and the oily material dissolved in 150 mL of methylene chloride. The organic layer was washed with water and dried on anhydrous sodium sulfate. The solvent was evaporated under reduced pressure and purified on silica gel column using 10% ethyl acetate/ hexanes. The desired fractions were combined and the solvent was evaporated to give an oil, yield 3.5 parts. $^1$H NMR confirmed the following structure. The reaction proceeded as follows:

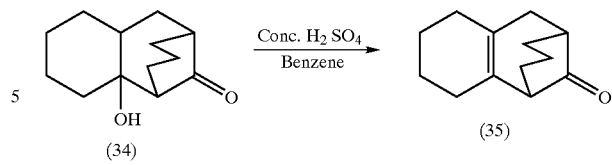

(c) Synthesis of (3-tert-butyldimethylsiloxyphenyl) methoxymethylene tricyclo[7.3.1.0$^{2,7}$]tridec-2,7-ene (36)

Into a 500 mL three-neck flask equipped with magnetic stirrer, pressure-equalizing addition funnel and nitrogen line was charged with 200 mL of anhydrous THF. Twelve parts of titanium tetrachloride was added dropwise over a period of 30 minutes. The suspension was stirred for 20 minutes and 17 parts of zinc was added in small portions. The reaction mixture was heated under reflux for 2 hours and 30 mL of triethylamine was added dropwise. After refluxing one hour, 4 parts of a solution of methyl 3-tert-butyldimethylsiloxybenzoate and 2 parts of ketone (35) in 35 mL of dry THF was added over a period of 60 minutes and the reaction mixture was heated for one hour. The mixture on TLC silia gel plate showed the presence of the starting ester. An additional 3.3 parts of starting ketone (35) in 35 mL of dry THF was added dropwise over 90 minutes and refluxed for two hours. The mixture was cooled to room temperature, diluted with 500 mL of hexane and decanted. The residue was washed with 3×200 mL of hexane. The combined hexane layer was filtered and evaporated under reduced pressure to give an oily material which was purified by chromatography on silica gel column using 2.5% ethyl acetate/hexane as an eluant. The fractions were checked by TLC on silica gel plate and the desired fractions were combined. The solvent was evaporated under reduced pressure to give an oil, yield 4.75 parts. The structure was confirmed by $^1$H NMR. The reaction proceeded as follows:

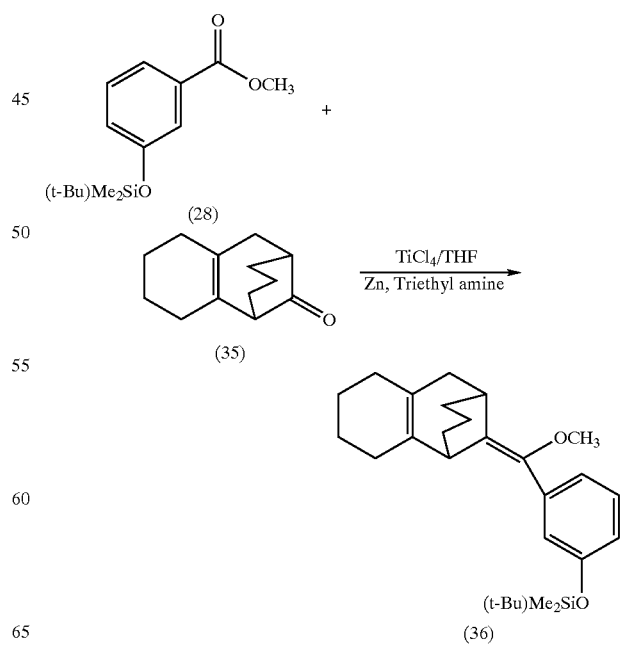

(d) Synthesis of (3-hydroxyphenyl) methoxymethylene tricyclo[7.3.1.0$^{2,7}$]tridec-2,7-ene (37)

To a crude solution of 10 parts of (3-tert-Butyldimethylsiloxyphenyl) methoxymethylene tricyclo [7.3.1.0$^{2,7}$]tridec-2,7-ene in 150 mL of THF was added 7 parts of 70% tetra-n-butylammonium fluoride in 50 mL of THF over a period of 10 minutes and stirring was continued for two hours. TLC on silica gel plate showed the formation of new product. Solvent was evaporated under reduced pressure and the oily material was dissolved in 300 mL of methylene chloride and washed with 2×150 mL of water. After drying over anhydrous sodium sulfate, the solvent was evaporated and the oily product was purified on silica gel column. TLC on silica gel plate of the fractions were checked and the combined organic solvent was evaporated, yield 3.60 parts. The structure of the product was confirmed on the basis of $^1$H NMR. The reaction proceeded as follows:

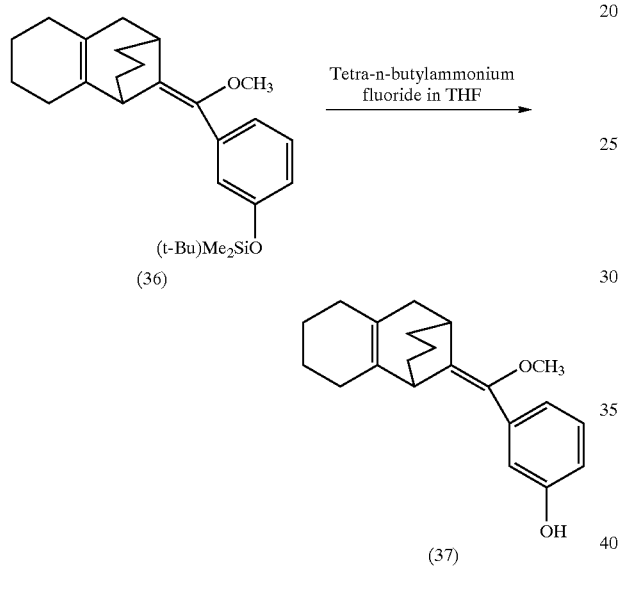

(e) Synthesis of (3-phosphoryloxyphenyl) methoxymethylene tricyclo[7.3.1.0$^{2,7}$]tridec-2,7-ene, Disodium Salt (38)

Into a 250 mL three-neck round bottom flask equipped with magenetic stirrer was added 15 mL of dry THF under nitrogen and then 1 mL of phosphorous oxychloride was added drop-wise (reaction flask was cooled in ice-water bath). A solution of 1 part of alkene (37) in 15 mL of THF containing 0.325 parts of anhydrous pyridine was added to the reaction flask over a period of 30 minutes. The reaction mixture was stirred at room temperature for 3 hours. TLC on silica gel plate showed the formation of new product. The solvent was evaporated to dryness and 10 mL of THF was added to the reaction flask. A solution containing 0.55 parts of 3-hydroxypropionitrile and 0.65 parts of anhydrous pyridine in 7.5 ml of dry THF was added dropwise to the reaction mixture over 25 minutes and was stirred for 15 hours at room temperature. The reaction was cooled to ice-water temperature and the solid was filtered and washed with cold THF. The solvent was evaporated and oily material was chromatographed on silica gel column using 70% ethyl acetate/hexane containing 0.1% triethyl amine. Fractions were checked by TLC on silica gel plate and the desired fractions were combined and evaporated under reduced pressure to give an oil, yield 1.20 parts. The oily material was dissolved in 15 mL of dry THF and a solution of 0.75 parts of sodium hydroxide in 5 mL of water was added drowise. Stirring was continued for two hours and the reaction mixture was diluted with 10 mL of acetonitrile. The solid was filtered and washed with acetonitrile. The soild material was crystallised with methanol and acetone mixture. The solid was filtered and washed with acetone and dried, to yield 0.85 parts. The structure was confirmed on the basis of $^1$H NMR. The reaction proceeded as follows:

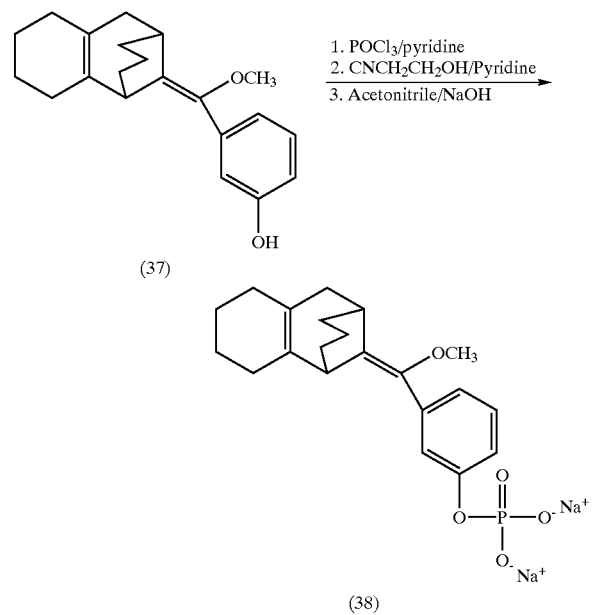

(f) Photooxidation of (3-phosphoryloxyphenyl) methoxymethylene tricyclo[7.3.1.0$^{2,7}$]tridec-2,7-ene, Disodium Salt (38)

Alkene (38) was photooxidized as reported above, to give [(4-Methoxy)-4-(3-phosphoryloxyphenyl)]Spiro [1,2-dioxetane-3,13'-tricyclo[7.3.1,o$^{2,7}$]tridec-2,7-ene], disodium salt (39).

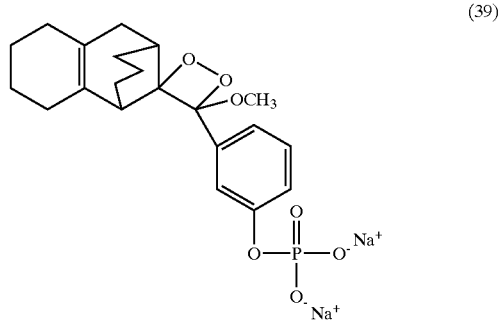

EXAMPLE III

This example illustrates the preparation of [(4-methoxy)-4-(3-phosphoryloxyphenyl]spiro[1,2-dioxetane-3,2'-adamantan-4,5-ene], disodium salt (46). The sequence of the reactions in accordance herewith:

(a) Synthesis of 5-Hydroxyadamantan-2-one (40)

Into a single neck 500 mL round bottom flask equipped with a magnetic stirrer and water bath, 75 parts of acetic acid containing 5 parts acetic anhydride was added. Twenty five parts of chromium trioxide was added in portions in 40 minutes while the temperature was maintained at 15–20° C. with water bath. Five parts of Adamantan-2-one was added in portions over a period of 15 minutes. Stirring was continued for one hour. The viscous reaction mixture was poured into cold 250 mL of aqueous 20% sodium hydroxide solution. The aqueous layer was extracted with 3×250 mL of ethyl acetate and washed with 2×250 mL of water and dried over sodium sulfate. Solvent was evaporated under reduced pressure and chromatographed on silica gel column using 75% ethyl acetate/hexane. The desired fractions were collected and solvent was evaporated to give a solid, yield 2.6 parts, single spot on silica gel TLC plate. The structure was confirmed on the basis of $^1$H NMR. The reaction proceeded as follows:

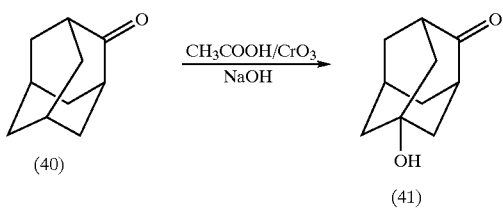

(b) Synthesis of adamantan-4,5-ene-2-one (42)

Into a 500 mL round bottom flask equipped with magnetic stirrer, Dean Stark water separator and a condenser, was added 150 mL of benzene and 5.5 parts of hydroxy ketone (41). The solid was dissolved by heating the flask at 40° C. and 0.5 parts of concentrated sulfric acid was added. The reaction mixture was refluxed for 18 hours. After cooling to room temperature the solvent was evaporated under reduced pressure and the oily material was dissolved in 200 mL of ethyl acetate. The organic layer was washed with water. The ethyl acetate layer was dried over sodium sulfate and evaporated under reduced pressure. The oily material was chromatographed on silica gel column using 7% ethyl acetate/hexane. The desired fractions were combined and the solvent was evaporated under reduced pressure to give an oil which on standing at 20° C., solidified, yield 4.5 parts. The structure of the product was confirmed on the basis of $^1$H NMR. The reaction proceeded as follows:

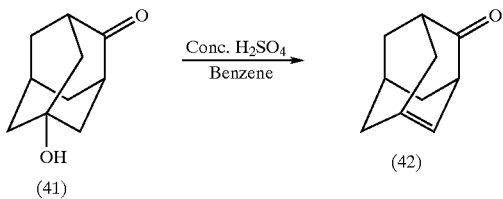

(c) Synthesis of (3-tert-butyldimethylsiloxyphenyl) methoxymethylene adamantan-4,5-ene (43)

Into a 500 mL three-necked flask equipped with magnetic stirrer, pressure-equalizing addition funnel and nitrogen line was charged with 200 mL of anhydrous THF. Fifteen parts of titanium tetrachloride was added dropwise over a period of 30 minutes. The suspension was stirred for 20 minutes and 22 parts of zinc was added in small portions. The reaction mixture was heated under reflux for 2 hours and 37 parts of triethylamine was added dropwise. After refluxing one hour, four parts of a solution of ester (28) and 3 parts of alkene (42) in 50 mL of dry THF was added over a period of 90 minutes and the reaction mixture was heated for one hour. Silica gel TLC plate analysis of the mixture showed the presence of starting ester (28). Additional 1.5 parts of starting ketone (42) in 15 mL of dry THF was added dropwise over 30 minutes and refluxed for two hours. The mixture was cooled to room temperature, diluted with 500 mL of hexane and decanated. The residue was washed with 3×200 mL of hexane. The combined hexane layer was filtered and evaporated under reduced pressure to give an oily material which was purified by chromatography on silica gel column using 2.5% ethyl acetate/hexane as an eluant. The fractions were checked by TLC on silica gel plate and the desired fractions were combined. The solvent was evaporated under reduced pressure to give an oil, yield 5.75 parts. The structure was confirmed by $^1$H NMR. The reaction proceeded as follows:

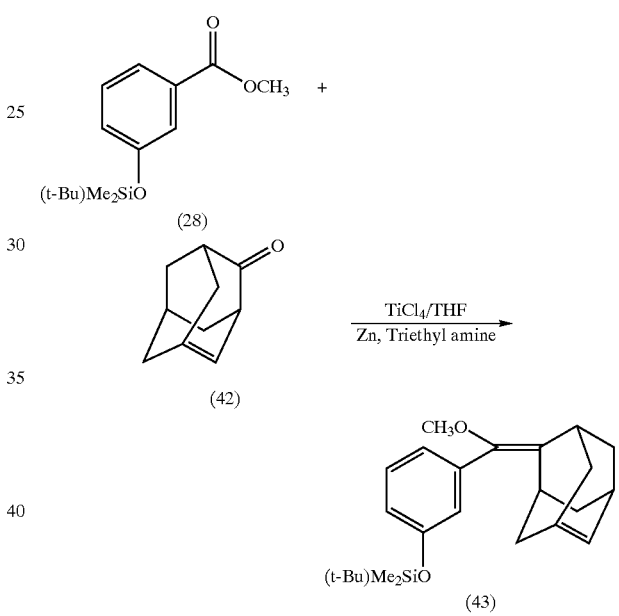

(d) Synthesis of (3-Hydroxyphenyl) methoxymethylene adamantan-4,5-ene (44)

A solution of 5.75 parts of the alkene (43) and 100 mL of THF was added to 7.0 parts of 70% of tetra-n-butylammonium fluoride in 50 mL of THF over a period of 15 minutes. Sirring was continued for two hours. TLC on silica gel plate showed the formation of new product. Solvent was evaporated under reduced pressure and the oily material was dissolved in 250 mL of methylene chloride and washed with 2×250 mL of water. After drying over anhydrous sodium sulfate, the solvent was evaporated and the oily product was purified on silica gel column. TLC on silica gel plate of the fractions were checked and the combined organic solvent was evaporated, yield 3.20 parts. The structure of the product was confirmed on the basis of $^1$H NMR. The reaction proceeded as follows:

23

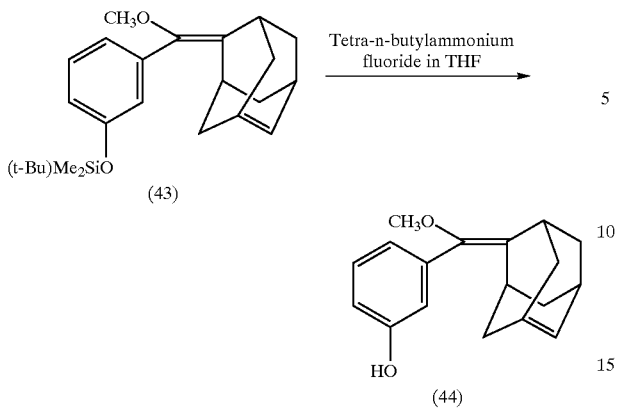

(e) Synthesis of (3-phosphoryloxyphenyl) methoxymethylene adamantan-4,5-ene, Disodium Salt (45)

Thirty parts of dry THF under nitrogen and 4.0 mL of phosphorous oxychloride was added dropwise to a 250 mL three-neck round bottom flask equipped with magenetic stirrer (reaction flask was cooled in an ice-water bath). A solution of 2.0 parts of alkene (44) in 25 mL of THF containing 0.725 parts of anhydrous pyridine was added to the reaction flask over a period of 30 minutes and stirring was continued at room temperature for 3 hours. TLC on silica gel plate showed the formation of new product. The solvent was evaporated to dryness and 20 mL of THF was added to the reaction flask. A solution containing 1.55 parts of 3-hydroxypropionitrile and 1.65 parts of anhydrous pyridine in 15 mL of dry THF was added to the reaction mixture dropwise over 25 minutes and stirring was continued for 15 hours at room temperature. The reaction was cooled to ice-water temperature and the solid was filtered, washed with cold THF. The solvent was evaporated and resulting oily material was chromatographed on silica gel column using 70% ethyl acetate/hexane containing 0.1% triethylamine. Fractions were checked by TLC on silica gel plate and desired fractions were combined and evaporated under reduced pressure to give an oil, yield 2.50 parts. The oily material was dissolved in 15 mL of dry THF and a solution of 1.75 parts of sodium hydroxide in 15 mL of water was added dropwise. Stirring was continued for two hours and the reaction mixture diluted with 20 mL of acetonitrile. The solid was filtered and washed with acetonitrile. The solid material was crystalized with methanol/acetone mixture. The solid was filtered and washed with acetone and dried, yield, 1.95 parts. The structure was confirmed on the basis of $^1$H NMR. The reaction proceeded as follows:

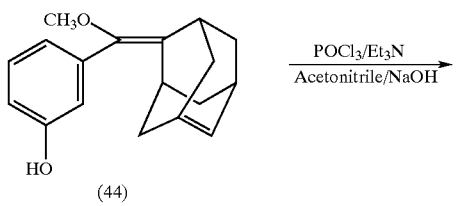

24

-continued

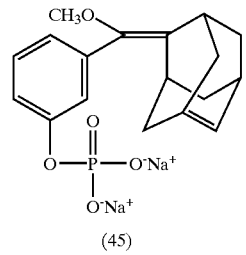

(f) Photooxidation of (3-phosphoryloxyphenyl) methoxymethylene adamantan-4,5-ene, Disodium Salt (45)

Alkene (45) was photooxidized as reported above, to give [(4-methoxy)-4-(3-phosphoryloxyphenyl]spiro[1,2-dioxetane-3,2'-adamantan-4,5-ene], disodium salt (46).

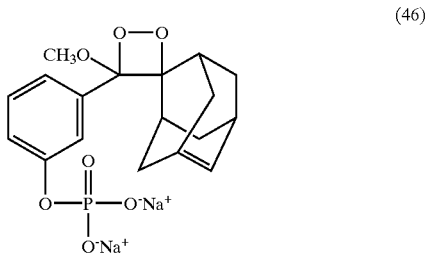

EXAMPLE IV

This example illustrates the preparation of [4-(2,2,2-trifluoroethoxy)-4-(3-phosphoryloxyphenyl)]spiro[1,2-dioxetane-3,13'-tricyclo[7.3.1.0$^{2,7}$]tridec-2,7-ene], disodium salt (52). The sequence of the reactions in accordance herewith:

(a) Synthesis of 2,2,2-trifluoroethyl 3-hydroxybenzoate (47)

Into a 250 mL round bottom flask equipped with magnetic stirrer and heating mantle was added 10 parts of 3-hydroxy benzoic acid, 100 parts of 2,2,2-trifluoroethanol and 0.5 parts of concentrated sulfuric acid. The reaction mixture was heated at 95° C. for 48 hours. The solvent was evaporated under reduced pressure and the solid material was dissolved in 250 mL of ethyl acetate. The organic layer was washed with 250 mL of water, 250 mL 5% solution of sodium bicarbonate in 100 mL of water and finally with 250 mL of water. The ethyl acetate layer was dried over anhydrous sodium sulfate and the solvent was evaporated under reduced pressure, yield 4.1 parts. TLC on silica gel plate showed a single spot. The structure was confirmed on the basis of $^1$H NMR. The reaction proceeded as follows:

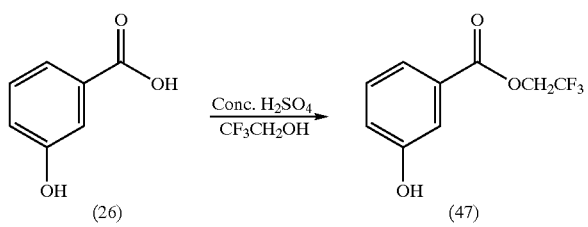

(b) Synthesis of 2,2,2-Trifluoroethyl 3-tert-butyldimethylsiloxybenzoate (48)

Into a 250 mL round bottom flask was added 30 mL of dry dimethyl formamide and 4.0 parts of ester (47) and 3.5 parts of tert-butyldimethyl silyl chloride were added to the reaction flask with stirring. Three parts of Imidazole was added in portions and stirring was continued for 10 hours. The reaction mixture was diluted with 80 mL of water and the product was extracted with ethyl acetate. The organic layer was washed with water and dried on anhydrous sodium sulfate. The solvent was evaporated under reduced pressure to give an oil, yield 5.65 parts. The structure was confirmed on the basis of $^1$H NMR. The reaction proceeded as follows:

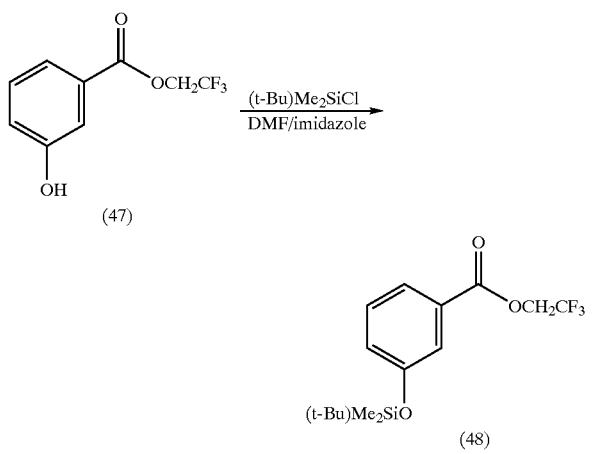

(c) Synthesis of (3-tert-Butyldimethylsiloxyphenyl)(2,2,2-trifluoroethoxy)methylene]tricyclo[7.3.1.0$^{2,7}$]tridec-2,7-ene (49)

Into a 500 mL three-neck flask equipped with magnetic stirrer, pressure-equalizing addition funnel and nitrogen line was charged with 200 parts of anhydrous THF. Ttitanium tetrachloride(20 mL) was added dropwise over a period of 30 minutes. The suspension was stirred for 20 minutes and 30 parts of zinc was added in small portions. The reaction mixture was heated under reflux for 2 hours and 50 parts of triethylamine was added dropwise. After refluxing one hour, 5.5 parts of a solution of ester (48) and 3.5 parts of ketone (35) in 40 mL of dry THF was added over a period of 90 minutes and the reaction mixture was heated for one hour. TLC on silica gel plate of the mixture showed the presence of starting ester. Two parts ketone (35) in 15 mL of dry THF was added dropwise over 30 minutes and refluxed for two hours. The mixture was cooled to room temperature, diluted with 500 mL of hexane and decanated. The residue was washed with 3×200 mL of hexane. The combined hexane layer was filtered and evaporated under reduced pressure to give an oily material which was purified by chromatography on silica gel column using 10% ethyl acetate/hexane mixture as an eluant. The fractions were checked by TLC on silica gel plate and the desired fractions were combined. The solvent was evaporated under reduced pressure to give an oil, yield 6.1 parts. The structure was confirmed by $^1$H NMR. The reaction proceeded as follows:

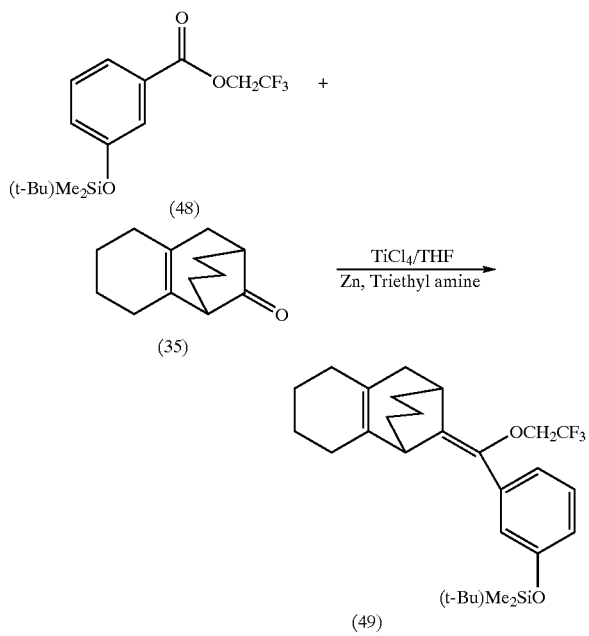

(d) Synthesis of [(3-Hydroxyphenyl)(2,2,2-trifluoroethoxy)methylene]tricyclo[7.3.1.0$^{2,7}$]tridec-2,7-ene (50)

To a solution 6.1 parts of alkene (49) in 100 mL of THF was added to 7.0 parts of 70% of tetra-n-butylammonium fluoridein 50 mL of THF over a period of 15 minutes and stirring was continued for two hours. TLC on silica gel plate showed the formation of new product. The solvent was evaporated under reduced pressure and the oily material was dissolved in 300 mL of ethyl acetate and washed with 2×200 mL of water. After drying over anhydrous sodium sulfate, the solvent was evaporated and the oily product was purified on silica gel column. TLC on silica gel plate of the fractions were checked and the combined organic solvent was evaporated, yield 3.9 parts. The structure of the product was confirmed on the basis of $^1$H NMR. The reaction proceeded as follows:

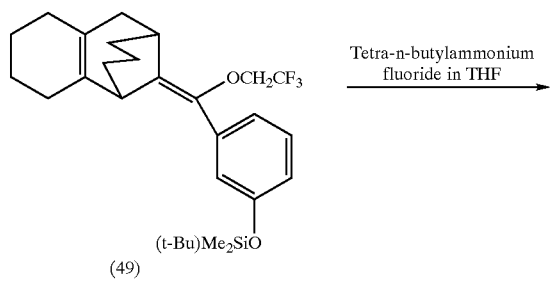

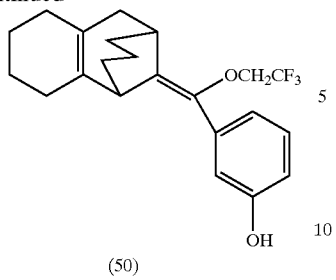

(50)

(e) Synthesis of [(3-Phosphoryloxyphenyl)(2,2,2-trifluoroethoxy)methylene]tricyclo[7.3.1.0$^{2,7}$]tridec-2,7-ene, Disodium Salt (51)

Into a 100 mL three-neck flask equipped with magnetic stirrer, under nitrogen was added 35 mL of methylene chloride and 2.75 parts of phosphorous oxychloride. The flask was cooled in an ice-water bath and 1.57 parts of pyridine added dropwise over a period of 20 minutes. Stirring was continued for 20 minutes and 3.5 parts of alkene (50) was dissolved in 35 mL of methylene chloride and added to the flask over a period of 30 minutes. The reaction mixture was stirred for three hours at room temperature and 3.56 parts of 2-cyanoethanol and 3.56 parts of pyridine in 35 mL of methylene chloride was added to the reaction flask. The reaction mixture was stirred for 48 hours. The solvent was evaporated and diluted with 150 mL of ethyl acetate. The solid was filtered and washed with 25 ml of ethyl acetate. The combined organic layer was washed with water and dried over sodium sulfate. The oily material was dissolved in 300 parts of acetone and 4 parts of sodium hydroxide in 6 parts of water was added dropwise. The solid was filtered and crystalized with methanol and a mixtue of ethyl acetate and ether to give 2.9 parts of white solid. The structure of the product was confirmed on the basis of $^1$H NMR. The reaction proceeded as follows:

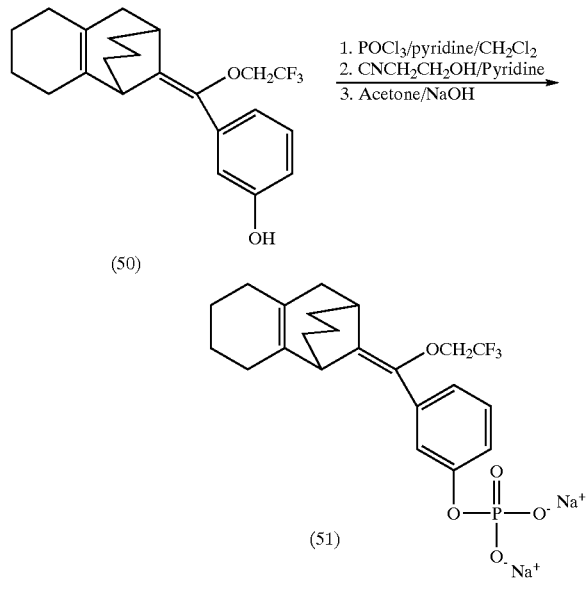

(f) Photooxidation of [(3-Phosphoryloxyphenyl)(2,2,2-trifluoroethoxy)methylene]tricyclo[7.3.1.0$^{2,7}$]tridec-2,7-ene, Disodium Salt (51)

Alkene (51) was photooxidized as reported above, to give [4-(2,2,2-trifluoroethoxy)-4-(3-phosphoryloxypheny)]spiro[1,2-dioxetane-3,2'-adamantane], Disodium Salt (52).

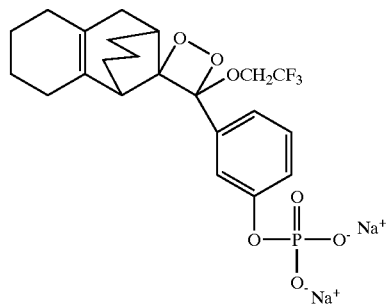

EXAMPLE V

This example illustrates the preparation of [4-(2-phenoxyethoxyl)-4-(3-phosphoryloxyphenyl)spiro[1,2-dioxetane-3,2'-adamantane], disodium salt (58). The sequence of the reactions in accordance herewith:

(a) Synthesis of 2-Phenoxyethyl 3-hydroxybenzoate (53)

Into a 250 mL round bottom flask equipped with magnetic stirrer and heating mantle was added 16.0 parts of 3-hydroxy benzoic acid, 100 parts of 2-phenoxyethanol and 0.5 parts of concentrated sulfuric acid. The reaction mixture was heated at 95° C. for 48 hours. The excess of 2-phenoxyethanol was evaporated under reduced pressure at 90° C. The solid material was dissolved in 250 mL of ethyl acetate. The organic layer was first washed with 200 mL of water, second with 250 mL of 5% solution of sodium bicarbonate in water and finally washed with 3×250 mL of water. The ethyl acetate layer was dried over anhydrous sodium sulfate and the solvent was evaporated under reduced pressure. This material was purified by chromatography on silica gel using 20% ethyl acetate/hexane. The desired fractions were combined and solvent was evaporated to give an oily material which on treatment with hexane gave a solid, yield 5.1 parts. TLC on silica gel plate showed single spot. The structure of the product was confirmed on the basis of $^1$H NMR. The reaction proceeded as follows:

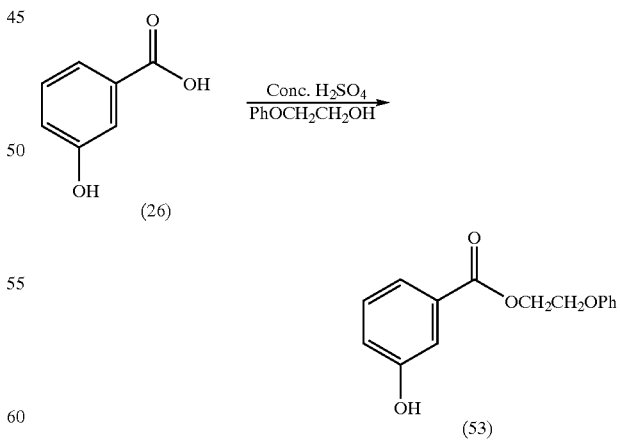

(b) Synthesis of 2-phenoxyethyl 3-tert-butyldimethylsiloxybenzoate (54)

Into a 250 mL round bottom flask was added 30 mL of dry dimethyl formamide. Five parts of hydroxy ester (53) and 3.5 parts of tert-butyldimethyl silyl chloride were added. to the reaction flask with stirring. Three parts of Imidazole was added in portions and stirring was continued for 10 hours. The reaction mixture was diluted with 80 mL of water and the product was extracted with ethyl acetate. The organic layer was washed with water and dried on anhydrous sodium sulfate. The solvent was evaporated under reduced pressure to give an oil, yield 6.80 parts. This material was pure enough for next step of the reaction. The reaction proceeded as follows:

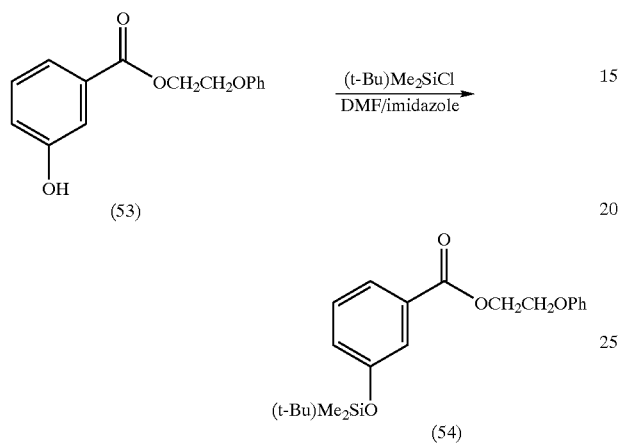

(c) Synthesis of [(3-tert-Butyldimethylsiloxyphenyl)(2-phenoxyethoxy)methylene]adamantane (55)

Into a 500 mL three-neck flask equipped with magnetic stirrer, pressure-equalizing addition funnel and nitrogen line was charged with 200 mL anhydrous THF. Fifteen parts of titanium tetrachloride was added dropwise over a period of 30 minutes. After stirring the suspension for 20 minutes, 22 parts of zinc was added in small portions. The reaction mixture was heated under reflux for 2 hours and 37 mL of triethylamine was added dropwise. After refluxing one hour a solution 5.9 parts of alkene (54) and 3.0 parts of adamantan-2-one in 40 mL of dry THF was added over a period of 90 minutes. The reaction mixture was heated for one hour. TLC on silica gel plate of the mixture showed the presence of starting ester. One and a half part of Adamantan-2-one in 20 mL of dry THF was added dropwise over 30 minutes and refluxed for two hours. The mixture was cooled to room temperature, diluted with 500 mL of hexane and decanated. The residue was washed three times with 200 mL of hexane. The combined hexane layer was filtered and evaporated under reduced pressure to give an oily material which was purified by chromatography on silica gel column using 2.5% ethyl acetate/hexane as an eluant. The fractions were checked by TLC on silica gel plate and the desired fractions were combined. The solvent was evaporated under reduced pressure to give an oil, yield 6.30 parts. The structure was confirmed by ¹H NMR. The reaction proceeded as follows:

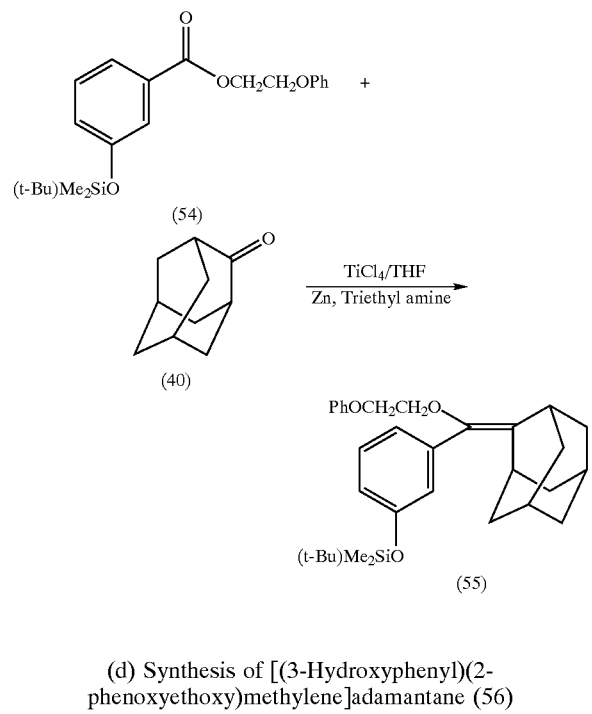

(d) Synthesis of [(3-Hydroxyphenyl)(2-phenoxyethoxy)methylene]adamantane (56)

To a solution of 6.30 parts of alkene (55) in 100 mL of THF was added 7.0 parts of 70% mixture of tetra-n-butylammonium fluoride in 50 mL of THF over a period of 15 minutes. The reaction mixture was stirred for two hours. TLC on silica gel plate showed the formation of new product. The solvent was evaporated under reduced pressure and the oily material was dissolved in 300 mL of ethyl acetate and washed with two times with 200 mL of water. After drying over anhydrous sodium sulfate, the solvent was evaporated and the oily product was purified on silica gel column. TLC on silica gel plate of the fractions were checked and the combined organic solvent was evaporated, yield 3.75 parts. The structure of the product was confirmed on the basis of ¹H NMR. The reaction proceeded as follows:

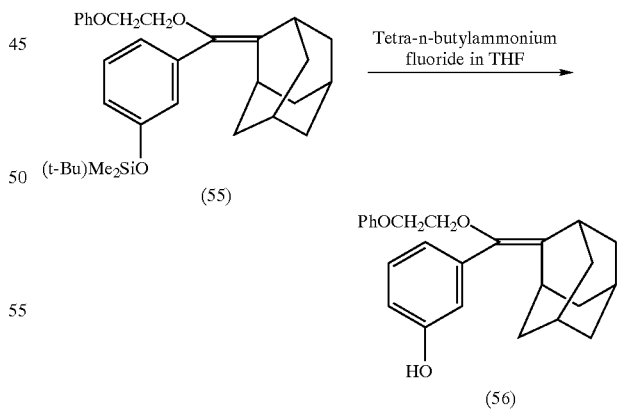

(e) Synthesis of [(3-Phosphoryloxyphenyl)(2-phenoxyethoxy)methylene]adamantane, Disodium Salt (57)

Into a 100 mL three-neck flask equipped with magnetic stirred under nitrogen was added 10 mL of anhydrous pyridine. The flask was cooled in a ice-water bath and 4 mL of phosphorous oxychloride was added dropwise over a period of 20 minutes. The reaction mixture was stirred for 20 minutes. Two parts of alkene (56) was dissolved in 10 parts of pyridine and added to the flask over a period of 30 minutes. The reaction mixture was stirred for two hours at room temperature. This material was poured carefully into 15.0 parts of sodium hydroxide in 50 mL of water containing 70.0 g of crushed ice. The stirring was continued for 15 hours. Solid was filtered and washed with acetone. The solid material was crystalized with methanol and acetone, yield 1.35 parts. The reaction proceeded as follows:

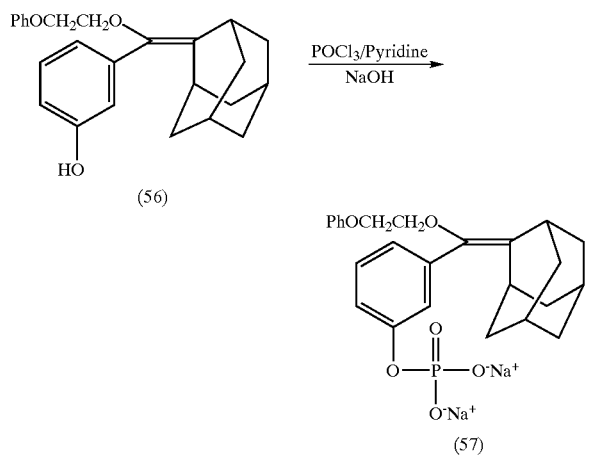

(f) Photooxidation of [(3-Phosphoryloxyphenyl)(2-phenoxyethoxy)methylene]adamantane, Disodium Salt (57)

Alkene (57) was photooxidized as reported above, to give [4-(2-phenoxyethoxyl)-4-(3-phosphoryloxyphenyl)]spiro[1,2-dioxetane-3,2'-adamantane], disodium salt (58).

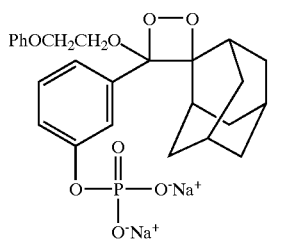

EXAMPLE VI

This example illustrates the preparation of [4-(2-phenoxyethoxyl)-4-(3-phosphoryloxyphenyl)spiro[1,2-dioxetane-3 13'-tricyclo[7.3.1.0$^{2,7}$]tridec-2,7-ene], disodium salt (62). The sequence of the reactions in accordance herewith:

(a) Synthesis of [(3-tert-Butyldimethylsiloxyphenyl)(2-phenoxyethoxy)methylene]tricyclo[7.3.1.0$^{2,7}$] tridec-2,7-ene (59)

Into a 1000 mL three-neck flask equipped with magnetic stirrer, pressure-equalizing addition funnel and nitrogen line was charged with 300 mL anhydrous THF. Twenty two parts of titanium tetrachloride was added dropwise over a period of 30 minutes. After stirring the suspension for 20 minutes, 34 parts of zinc was added in small portions. The reaction mixture was heated under reflux for 2 hours and 57 mL of triethylamine was added dropwise. After refluxing one hour a solution 10 parts of ester (54) and 6.2 parts of ketone (35) in 60 mL of dry THF was added over a period of 60 minutes. The reaction mixture was heated for one hour. TLC on silica gel plate of the mixture showed the presence of starting ester. Two and a half parts of ketone (35) in 25 mL of dry THF was added dropwise over 40 minutes and refluxed for two hours. The mixture was cooled to room temperature, diluted with 1000 mL of hexane and decanated. The residue was washed three times with 250 mL of hexane. The combined hexane layer was filtered and evaporated under reduced pressure to give an oily material which was purified by chromatography on silica gel column using 10% ethyl acetate/hexane as an eluant. The fractions were checked by TLC on silica gel plate and the desired fractions were combined. The solvent was evaporated under reduced pressure to give an oil, yield 10.8 parts. Silica gel TLC shows single spot. The reaction proceeded as follows:

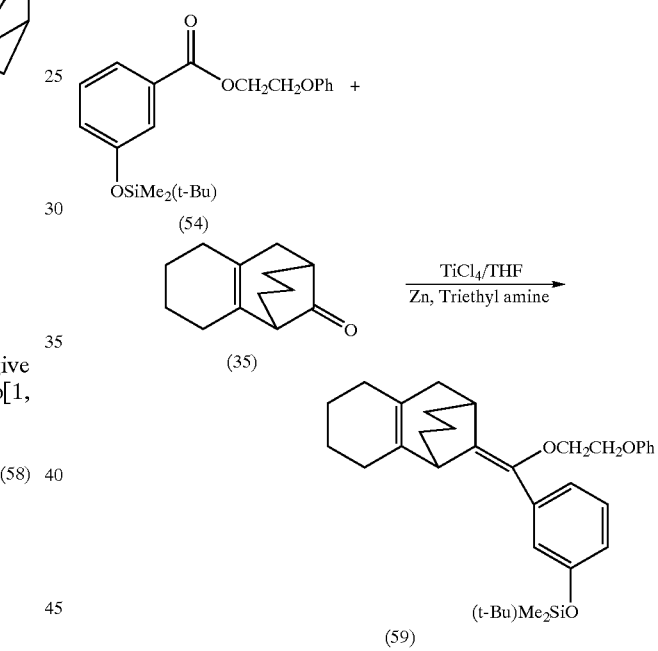

(b) Synthesis of [(3-Hydroxyyphenyl)(2-phenoxyethoxy)methylene]tricyclo[7.3.1.0$^{2,7}$]tridec-2,7-ene (60)

To a solution of 10.8 parts of alkene (59) in 150 mL of THF was added 10 parts of 70% mixture of tetra-n-butylammonium fluoride in 60 mL of THF over a period of 15 minutes. The reaction mixture was stirred for two hours. TLC on silica gel plate showed the formation of new product. The solvent was evaporated under reduced pressure and the oily material was dissolved in 350 mL of ethyl acetate and washed with two times with 200 mL of water. After drying over anhydrous sodium sulfate, the solvent was evaporated and the oily product was purified on silica gel column. TLC on silica gel plate of the fractions were checked and the combined organic solvent was evaporated, to yield 6.0 parts. The structure of the product was confirmed on the basis of $^1$H NMR. The reaction proceeded as follows:

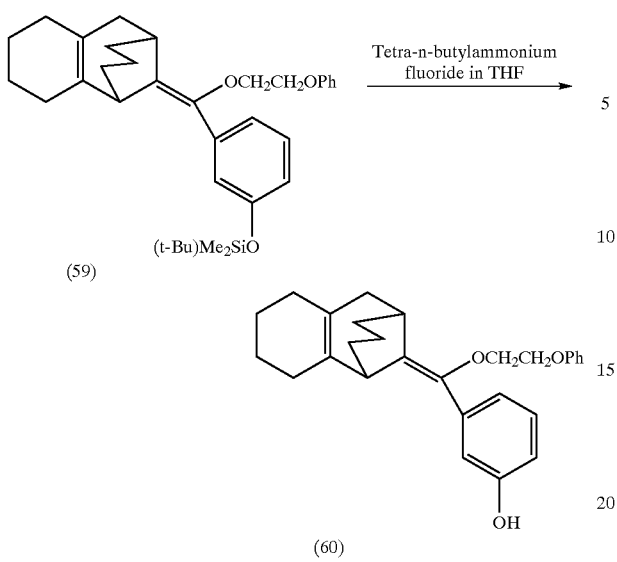

(59)

(60)

(c) Synthesis of [(3-Phosphoryloxyphenyl)(2-phenoxyethoxy)methylene]tricyclo[7.3.1.0$^{2,7}$]tridec-2,7-ene, Disodium Salt (61)

Into a 100 mL three-neck flask equipped with magnetic stirrer, under nitrogen was added 45 mL of methylene chloride and 4.57 parts of phosphorous oxychloride. The flask was cooled in an ice-water bath and 2.607 parts of pyridine in 45 mL of methylene chloride added dropwise over a period of 20 minutes. Stirring was continued for 20 minutes and 6.0 parts of alkene (60) was dissolved in 45 mL of methylene chloride and added to the flask over a period of 30 minutes. The reaction mixture was stirred for three hours at room temperature and 5.94 parts of 2-cyanoethanol and 5.94 parts of pyridine in 45 mL of methylene chloride was added to the reaction flask. The reaction mixture was stirred for 48 hours. The solvent was evaporated and diluted with 250 mL of ethyl acetate. The solid was filtered and washed with 50 ml of ethyl acetate. The combined organic layer was washed with water and dried over sodium sulfate. The oily material was dissolved in 600 parts of acetone and 8 parts of sodium hydroxide in 12.5 parts of water was added dropwise. The solid was filtered and crystalized with methanol and a mixture of ethyl acetate and ether to give 7.5 parts of white solid. The structure of the product was confirmed on the basis of $^1$H NMR. The reaction proceeded as follows:

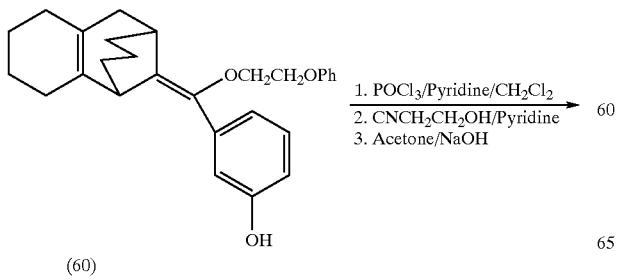

(60)

(d) Photooxidation of [(3-Phosphoryloxyphenyl)(2-phenoxyethoxy)methylene]tricyclo[7.3.1.0$^{2,7}$]tridec-2,7-ene, Disodium Salt (61)

Alkene (61) was photooxidized as reported above, to give [4-(2-phenoxyethoxyl)-4-(3-phosphoryloxyphenyl)]spiro[1,2-dioxetane-3 13'-tricyclo[7.3.1.0$^{2,7}$]tridec-2,7-ene], disodium salt (62).

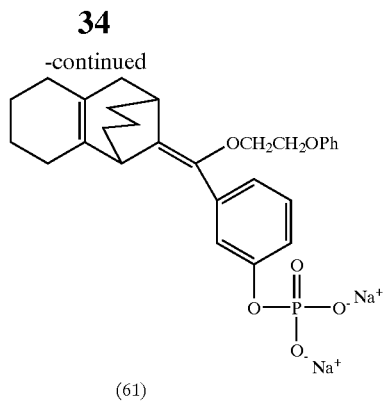

(61)

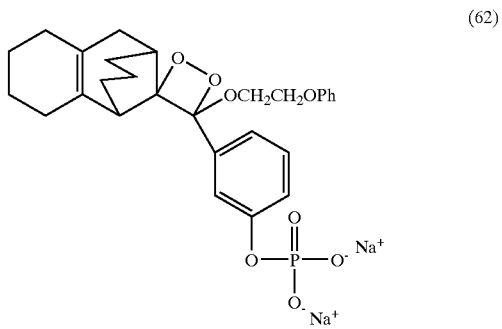

(62)

EXAMPLE VII

This example illustrates the preparation of [4-(2-phenoxyethoxyl)-4-(3-phosphoryloxyphenyl)spiro[1,2-dioxetane-3,2'-5-chloro-adamantane], disodium salt (58). The sequence of the reactions in accordance herewith:

(a) Synthesis of 5-chloroadamantan-2-one (63)

In a round bottom flask 6 parts of 5-hydroxyadamantan-2-one was dissolved in 36 mL of thionylchloride and boiled under refluxed for two hours. The excess thionyl chloride was evaporated. The residue was dissolved in 100 mL of methylene chloride and washed with 0.5N sodium hydroxide and then 10% aqueous sodium chloride solution. The organic layer was dried on sodium sulfate and the solvent evaporated under reduced pressure to give a white solid, yield 6.7 g. The reaction proceed as follows:

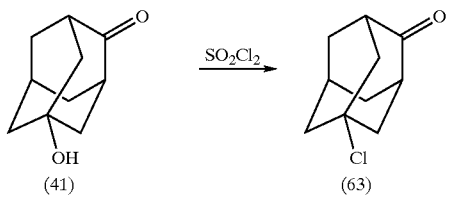

(41)   (63)

(b) Synthesis of [(3-tert-Butyldimethylsiloxyphenyl)(2-phenoxyethoxy)methylene]-5-chloroadamantane (64)

Into a 500 mL three-neck flask equipped with magnetic stirrer, pressure-equalizing addition funnel and nitrogen line was charged with 150 mL anhydrous THF. Titanium tetrachloride (12 mL) was added dropwise over a period of 30 minutes. After stirring the suspension for 20 minutes, 18 parts of zinc was added in small portions. The reaction mixture was heated under reflux for 2 hours and 29 mL of triethylamine was added dropwise. After refluxing one hour a solution 5.0 parts of ester (54) and 3.0 parts of 5-chloroadamantan-2-one in 35 mL of dry THF was added over a period of 45 minutes. The reaction mixture was heated for one hour. TLC on silica gel plate of the mixture showed the presence of starting ester. One part of 5-chloroadamantan-2-one in 20 mL of dry THF was added dropwise over 30 minutes and refluxed for two hours. The mixture was cooled to room temperature, diluted with 400 mL of hexane and decanated. The residue was washed three times with 150 mL of hexane. The combined hexane layer was filtered and evaporated under reduced pressure to give an oily material which was purified by chromatography on silica gel column using 5% ethyl acetate/hexane as an eluant. The fractions were checked by TLC on silica gel plate and the desired fractions were combined. The solvent was evaporated under reduced pressure to give an oil, yield 4.9 parts. The structure was confirmed by $^1$H NMR. The reaction proceeded as follows:

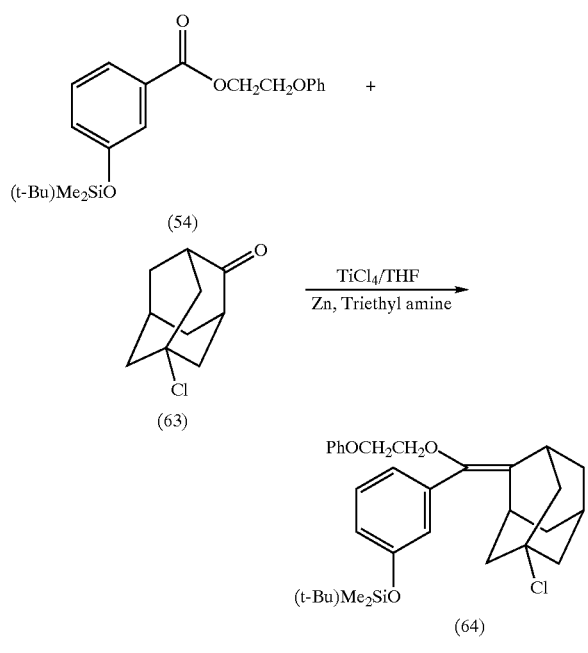

(c) Synthesis of [(3-Hydroxyphenyl)(2-phenoxyethoxy)methylene]-5-chloroadamantane (65)

To a solution of 4.9 parts of alkene (64) in 75 mL of THF was added 5.0 parts of 70% mixture of tetra-n-butylammonium fluoride in 25 mL of THF over a period of 15 minutes. The reaction mixture was stirred for two hours. TLC on silica gel plate showed the formation of new product. The solvent was evaporated under reduced pressure and the oily material was dissolved in 150 mL of ethyl acetate and washed with two times with 200 mL of water. After drying over anhydrous sodium sulfate, the solvent was evaporated and the oily product was purified on silica gel column. TLC on silica gel plate of the fractions were checked and the combined organic solvent was evaporated, yield 2.5 parts. The structure of the product was confirmed on the basis of $^1$H NMR. The reaction proceeded as follows:

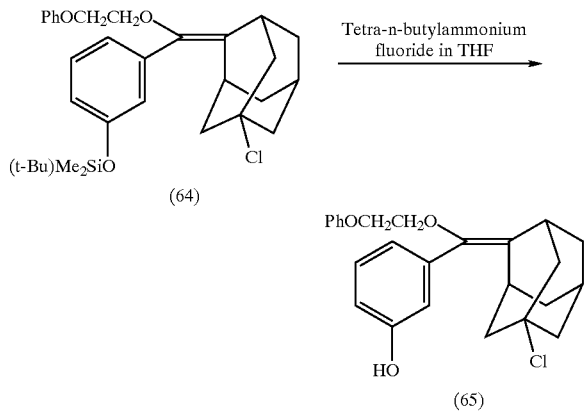

(d) Synthesis of [(3-Phosphoryloxyphenyl)(2-phenoxyethoxy)methylene]-5-chloroadamantane, Disodium Salt (66)

Into a 100 mL three-neck flask equipped with magnetic stirrer, under nitrogen was added 25 mL of methylene chloride and 1.53 parts of phosphorous oxychloride. The flask was cooled in an ice-water bath and 0.87 parts of pyridine in 10 mL of methylene chloride added dropwise over a period of 10 minutes. Stirring was continued for 20 minutes and 6 parts of alkene (65) was dissolved in 25 mL of methylene chloride and added to the flask over a period of 30 minutes. The reaction mixture was stirred for three hours at room temperature and 2.0 parts of 2-cyanoethanol and 2.0 parts of pyridine in 25 mL of methylene chloride was added to the reaction flask. The reaction mixture was stirred for 48 hours. The solvent was evaporated and diluted with 100 mL of ethyl acetate. The solid was filtered and washed with 50 ml of ethyl acetate. The combined organic layer was washed with water and dried over sodium sulfate. The oily material was dissolved in 150 parts of acetone and 2 parts of sodium hydroxide in 4 parts of water was added dropwise. The solid was filtered and crystalized with methanol and a mixtue of ethyl acetate and ether to give 2.6 parts of white solid. The structure of the product was confirmed on the basis of $^1$H NMR. The reaction proceeded as follows:

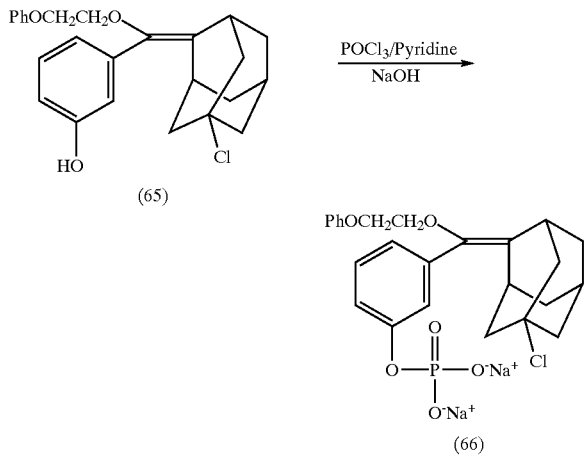

(e) Photooxidation of [(3-Phosphoryloxyphenyl)(2-phenoxyethoxy)methylene]-5-chloroadamantane, Disodium Salt (66)

Alkene (66) was photooxidized as reported above, to give [4-(2-phenoxyethoxyl)-4-(3-phosphoryloxyphenyl)]spiro[1,2-dioxetane-3,2'-5-chloroadamantane], disodium salt (67).

(67)

[Structure: PhOCH₂CH₂O-substituted phenyl dioxetane spiro adamantane with phosphate disodium salt and Cl]

EXAMPLE VIII

This example illustrates the preparation of [(4-Methoxy)-4-(3-phosphoryloxy-4-chlorophenyl)]Spiro [1,2-dioxetane-3,13'-tricyclo[7.3.1,o$^{2,7}$]tridec-2,7-ene], disodium salt (74). The sequence of the reactions in accordance herewith:

(a) Synthesis of methyl 4-chloro-3-hydroxybenzoate (68)

In a 250 mL round bottom flask 5 parts of 4-chloro-3-hydroxybenzoic acid was dissolved in 100 mL of methanol and 25 drops of concentrated sulfuric acid was added. The reaction mixture was heated under refluxed for 24 hours. TLC on silica gel shows the formation of new product. The solvent was evaporated and solid was dissolved in 150 mL of ethyl acetate. The organic layer was washed with 100 ml of 5% solution of sodium bicarbonate and dried over sodium sulfate. The solvent was evaporated under reduced pressure to give a white solid, yield 5.0 g.

[Structure (68): 4-chloro-3-hydroxybenzoic acid] → Conc. H₂SO₄ / CH₃OH → [Structure (69): methyl 4-chloro-3-hydroxybenzoate]

(b) Synthesis of methyl 3-tert-butyldimethylsiloxy-4-chlorobenzoate (70)

Into a 250 mL round bottom flask was added 40 mL of dry dimethyl formamide. Five parts of benzoate (69) and 4.86 parts of tert-butyldimethyl silyl chloride were added to the reaction flask with stirring. 4.04 parts of Imidazole was added in portions and stirring was continued for 12 hours. The reaction mixture was diluted with 50 mL water and extracted with 200 mL of ethyl acetate. The organic layer was washed twice with 100 mL of water and dried on anhydrous sodium sulfate. The solvent was evaporated under reduced pressure to give an oil, yield 7.1 parts. This material was pure enough for the next step of the reaction. The material was prepared according to the following:

[Structure (69)] → (t-Bu)Me₂SiCl / DMF/imidazole → [Structure (70): methyl 3-tert-butyldimethylsiloxy-4-chlorobenzoate]

(c) Synthesis of (3-tert-butyldimethylsiloxy-4-chlorophenyl)methoxymethylene tricyclo[7.3.1.0$^{2,7}$]tridec-2,7-ene (71)

Into a 500 mL three-neck flask equipped with magnetic stirrer, pressure-equalizing addition funnel and nitrogen line was charged with 150 mL of anhydrous THF. Ttitanium tetrachloride (12 mL) was added dropwise over a period of 30 minutes. The suspension was stirred for 20 minutes and 18 parts of zinc was added in small portions. The reaction mixture was heated under reflux for 2 hours and 29 mL of triethylamine was added dropwise. After refluxing one hour, 6 parts of a solution of methyl 3-tert-butyldimethylsiloxy4-chlorobenzoate and 4 parts of ketone (35) in 35 mL of dry THF was added over a period of 60 minutes and the reaction mixture was heated for one hour. The mixture on TLC silia gel plate showed the presence of the starting ester. An additional 2.5 parts of starting ketone (35) in 35 mL of dry THF was added dropwise over 45 minutes and refluxed for two hours. The mixture was cooled to room temperature, diluted with 500 mL of hexane and decanted. The residue was washed with 3×200 mL of hexane. The combined hexane layer was filtered and evaporated under reduced pressure to give an oily material which was purified by chromatography on silica gel column using 5% ethyl acetate/hexane as an eluant. The fractions were checked by TLC on silica gel plate and the desired fractions were combined. The solvent was evaporated under reduced pressure to give an oil, yield 5.6 parts. The structure was confirmed by $^1$H NMR. The reaction proceeded as follows:

[Structure (70)] + [Structure (35): ketone] → TiCl₄/THF, Zn, Triethyl amine →

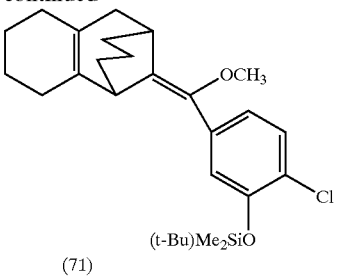

(71)

(d) Synthesis of (3-hydroxy-4-chlorophenyl) methoxymethylene tricyclo[7.3.1.0²,⁷]tridec-2,7-ene (72)

To a crude solution of 5.6 parts of (3-tert-Butyldimethylsiloxy-4-chlorophenyl) methoxymethylene tricyclo[7.3.1.0²,⁷]tridec-2,7-ene in 100 mL of THF was added 7 parts of 70% tetra-n-butylammonium fluoride in 30 mL of THF over a period of 10 minutes and stirring was continued for two hours. TLC on silica gel plate showed the formation of new product. Solvent was evaporated under reduced pressure and the oily material was dissolved in 200 mL of methylene chloride and washed with 2×100 mL of water. After drying over anhydrous sodium sulfate, the solvent was evaporated and the oily product was purified on silica gel column. TLC on silica gel plate of the fractions were checked and the combined organic solvent was evaporated, yield 3.25 parts. The structure of the product was confirmed on the basis of ¹H NMR. The reaction proceeded as follows:

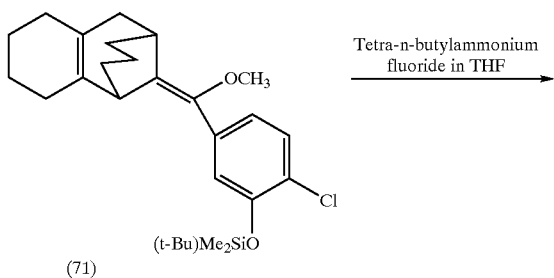

(e) Synthesis of (3-phosphoryloxy-4-chlorophenyl) methoxymethylene tricyclo [7.3.1.0²,⁷]tridec-2,7-ene, Disodium Salt (73)

Into a 100 mL three-neck round bottom flask equipped with magenetic stirrer was added 15 mL of dry methylene chloride under nitrogen and then 1.57 mL of phosphorous oxychloride was added dropwise (reaction flask was cooled in ice-water bath ) A solution of 3.0 parts of alkene (72) in 15 mL of methylene chloride containing 1.57 parts of anhydrous pyridine was added to the reaction flask over a period of 30 minutes.The reaction mixture was stirred at room temperature for 3 hours. TLC on silica gel plate showed the formation of new product. A solution containing 3.56 parts of 3-hydroxypropionitrile and 3.56 parts of anhydrous pyridine in 35 ml of methylene chloride was added dropwise to the reaction mixture over 25 minutes and was stirred for 15 hours at room temperature. The reaction was cooled to ice-water temperature and the solid was filtered, washed with cold methylene chloride. The solvent was evaporated and oily material was chromatographed on silica gel column using 70% ethyl acetate/hexane containing 0.1% triethyl amine. Fractions were checked by TLC on silica gel plate and the desired fractions were combined and evaporated under reduced pressure to give an oil. The oily material was dissolved in 150 mL of acetone and a solution of 2.5 parts of sodium hydroxide in 5 mL of water was added dropwise. Stirring was continued for two hours and the solid was filtered and washed with acetone. The soild material was crystalized with methanol and acetone mixture. The solid was filtered and washed with acetone and dried, yield 3.15 parts. The structure was confirmed on the basis of ¹H NMR. The reaction proceeded as follows:

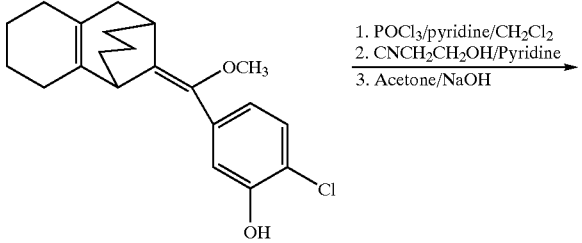

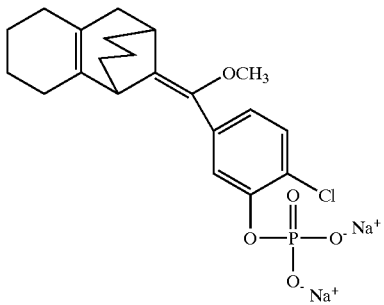

(f) Photooxidation of (3-phosphoryloxy-4-chlorophenyl)methoxymethylene tricyclo [7.3.1.0²,⁷]tridec-2,7-ene, Disodium Salt (73)

Alkene (73) was photooxidized as reported above to give [(4-Methoxy)-4-(3-phosphoryloxy-4-chlorophenyl)]Spiro [1,2-dioxetane-3,13'-tricyclo[7.3.1,0²,⁷]tridec-2,7-ene], disodium salt (74).

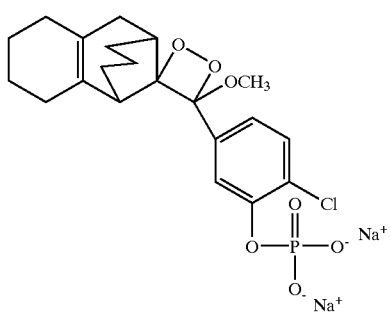

(74)

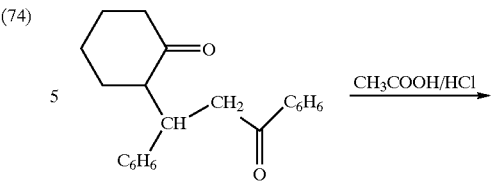

(76)

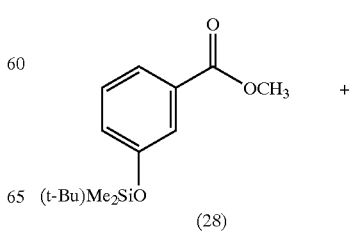

(77)

EXAMPLE IX

This example illustrates the preparation of [(4-Methoxy)-4-(3-phosphoryloxyphenyl)]Spiro[1,2-dioxetane-3,9-(2,4-diphenylbicyclo[3.3.1]non-2-ene)], disodium salt (81). The sequence of the reactions in accordance herewith:

(a). Synthesis of 2-(α-phenyl-β-benzoylethyl)-cyclohexanone (76)

Ten parts of benzalacetophenone and 5 parts of cyclohexanone was dissolved in 200 mL of ethyl alcohol and a solution of 5 parts of sodium hydroxide in 100 ml of ethanol was added to the reaction mixture. After 30 minutes the solution became cloudy and white solid was appeared. The reaction mixture was stirred for 10 hours at room temperature and solid was filtered, washed with water and then with 100 ml of ethyl alcohol. The white solid was dried under reduced pressure, with a yield of 12 parts. The reaction proceeded as follows:

(b). Synthesis of 2,4-Diphenyl bicyclo[3.3.1]non-2-ene-9one (77)

Into a 1 L round bottom flask fifteen parts of 2-(α-phenyl-β-benzoylethyl)-cyclohexanone, 500 ml acetic acid and 100 mL of concentrated hydrochloric acid was added. Reaction mixture was heated under reflux for 45 hours. The hot reaction mixture was diluted with 250 ml of water (reaction mixture was cloudy). The reaction mixture was cool to room temperature to give a white solid which was filtered and dried under vacuum, to yield 11.75 g of product. The reaction proceeded as follows:

(c) Synthesis of (3-tert-Butyldimethylsiloxyphenyl) methoxymethylene-2,4-diphenyl bicyclo[3.3.1]non-2-ene (78)

Into a 1000 mL three-neck flask equipped with magnetic stirrer, pressure-equalizing addition funnel and nitrogen line was charged with 200 mL of anhydrous THF. Ttitanium tetrachloride (17 mL) was added dropwise over a period of 30 minutes. The suspension was stirred for 20 minutes and 25.5 parts of zinc was added in small portions. The reaction mixture was heated under reflux for 2 hours and 42.5 mL of triethylamine was added dropwise. After refluxing one hour, 9 parts of a solution of methyl 3-tert-butyldimethylsiloxybenzoate and 4 parts of ketone (77) in 100 mL of dry THF was added over a period of 60 minutes and the reaction mixture was heated for one hour. The mixture on TLC silica gel plate showed the presence of the starting ester. An additional 1 part of starting ketone (77) in 35 mL of dry THF was added dropwise over 45 minutes and refluxed for two hours. The mixture was cooled to room temperature, diluted with 600 mL of hexane and decanted. The residue was washed with 3×250 mL of hexane. The combined hexane layer was filtered and evaporated under reduced pressure to give an oily material which was purified by chromatography on silica gel column using 5% ethyl acetate/hexane as an eluant. The fractions were checked by TLC on silica gel plate and the desired fractions were combined. The solvent was evaporated under reduced pressure to give an oil, yield 9.6 parts.

The structure was confirmed by $^1$H NMR. The reaction proceeded as follows:

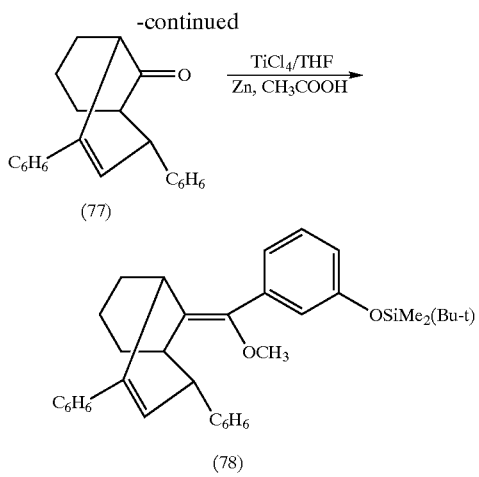

(c) Synthesis of (3-Hydroxyphenyl) methoxymethylene-2,4-diphenyl bicyclo[3.3.1]non-2-ene (79)

To a solution of 9.6 parts of (3-tert-Butyldimethylsiloxyphenyl) methoxy methylene-2,4-diphenyl bicyclo(3.3.1]non-2-ene (78) in 100 mL of THF was added 9 parts of 70% tetra-n-butylammonium fluoride in 30 mL of THF over a period of 10 minutes and stirring was continued for two hours. TLC on silica gel plate showed the formation of new product. Solvent was evaporated under reduced pressure and the oily material was dissolved in 300 mL of methylene chloride and washed with 2×100 mL of water. After drying over anhydrous sodium sulfate, the solvent was evaporated and the oily product was purified on silica gel column. TLC on silica gel plate of the fractions were checked and the combined organic solvent was evaporated, yield 6.24 parts. The structure of the product was confirmed on the basis of $^1$H NMR. The reaction proceeded as follows:

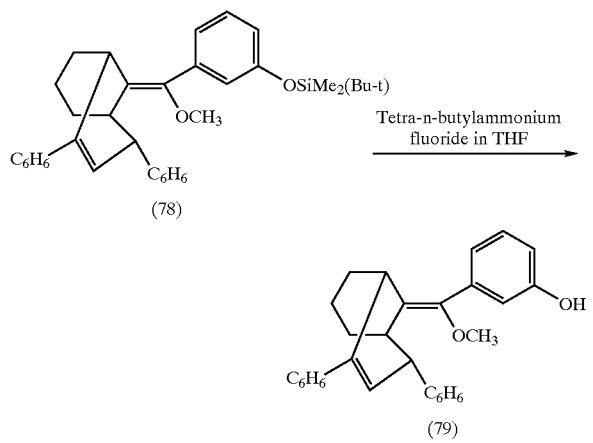

(d) Synthesis of (3-Phosphoryloxyphenyl) methoxymethylene-2,4-diphenyl bicyclo[3.3.1]non-2-ene, Disodium Salt (80)

Into a 100 mL three-neck round bottom flask equipped with magenetic stirrer was added 40 mL of dry methylene chloride under nitrogen and then 3.76 mL of phosphorous oxychloride was added drop-wise (reaction flask was cooled in ice-water bath). A solution of 5 parts of alkene (79) in 30 mL of methylene chloride containing 2.14 parts of anhydrous pyridine was added to the reaction flask over a period of 30 minutes. The reaction mixture was stirred at room temperature for 3 hours. TLC on silica gel plate showed the formation of new product. A solution containing 4.86 parts of 3-hydroxypropionitrile and 4.86 parts of anhydrous pyridine in 30 ml of methylene chloride was added dropwise to the reaction mixture over 25 minutes and was stirred for 48 hours at room temperature. The reaction was cooled to ice-water temperature and the solid was filtered, washed with cold methylene chloride. The solvent was evaporated and oily material was chromatographed on silica gel column using 70% ethyl acetate I hexane containing 0.1% triethyl amine. Fractions were checked by TLC on silica gel plate and the desired fractions were combined and evaporated under reduced pressure to give an oil. The oily material was dissolved in 300 mL of acetone and a solution of 7 parts of sodium hydroxide in 15 mL of water was added dropwise. Stirring was continued for two hours and the solid was filtered and washed with acetone. The soild material was crystalized with methanol and acetone mixture. The solid was filtered and washed with acetone and dried, yield 4.85 parts. The structure was confirmed on the basis of $^1$H NMR. The reaction proceeded as follows:

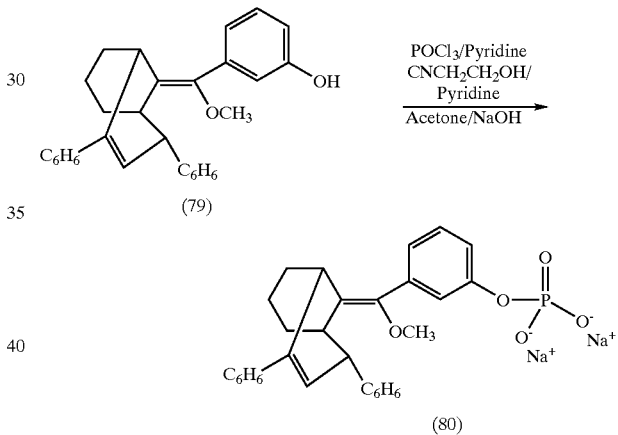

(e) Photooxidation of (3-Phosphoryloxyphenyl) methoxymethylene-2,4-diphenyl bicyclo[3.3.1]non-2-ene, Disodium Salt (80)

Alkene (80) was photooxidized as reported above, to give [(4-Methoxy)-4-(3-phosphoryloxyphenyl)]spiro[1,2-dioxetane-3,9'-(2,4-diphenylbicyclo(3.3.1]non-2-ene)], disodium salt (81).

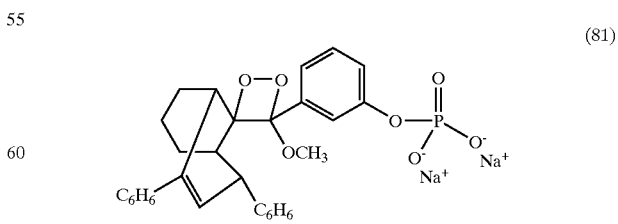

What is claimed is:
1. A stable 1,2-dioxetane selected from the group consisting of:

(a)
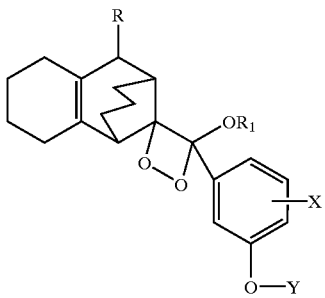

(b)
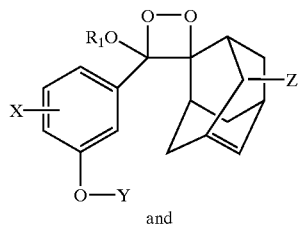
and (c)
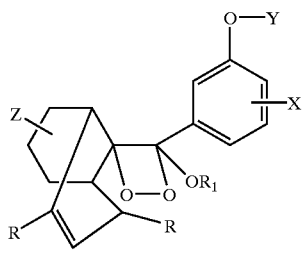

where $R_1$ is selected from the group consisting of alkyl, aryl, aralkyl, alkaryl, heteroalkyl, heteroaryl, cycloalkyl, cyclohetelroalkyl, alkyletheralkyl, alkyletheraryl, alkyl(etheralkyl)2, alkyl(etheralkyl)3, alkyletherhaloalkyl, alkyl(etherhaloalkyi)2, alkylalkene, alkylalkyne, arylalkene, arylalkyne, halogenated alkyl(mono, di, tri or any position in normal or branched or cyclic chain), alkylalcohol, alkylnitrile, alkylamine, alkylacid (mono or dibasic) or the inorganic salts thereof, haloalkylalcohol, haloalkylnitrile, haloalkylamine, haloalkylacid (mono or dibasic) or inorganic salts, linker-flourescent molecule, linker-antibodies, linker-antigen, linker-biotin, linker-avidin, linker-protein or linker-carbohydrates or linker-lipids; Y is a hydrogen, alkyl, acetate, t-butyldimethylsilyl or an enzyme cleaveable group or an antibody cleaveable group: R is hydrogen, alkyl or substituted alkyl, aryl or substituted aryl, alkylaryl or substituted alkylaryl, arylalkyl or substituted arylalkyl; X is chloro- or hydrogen and Z is hydrogen.

2. The 1,2dioxetane of claim 1, which is any of:

[(4-methoxy)4-(3-phosphoryloxyphenyl)]spiro[1,2 dioxetane-3,13'-(8-n-propyl)tricyclo[7.3.1.0$^{2,7}$]tridec-2,7-ene], disodium salt;

[(4-methoxy)4-(3-phosphoryloxyphenyl)]Spiro[1,2-dioxetane-3,13'-tricyclo[7.3.1,0$^{2,7}$]tridec-2,7-ene], disodium salt;

[(4methoxy)-4-(3-phosphoryloxyphenyl]spiro[1,2-dioxetane-3,2'-adamantan-4,5ene], disodium salt;

(4-(2,2,2-trifluoroethoxy)-4-(3-phosphoryloxyphenyl))spiro [1,2-dioxetane-3,13'-tricyclo[7.3.1.0$^{2,7}$]tridec-2,7-ene], disodium salt;

[4-(2-phenoxyethoxyl)-4-(3phosphoryloxyphenyl)spiro[1,2-dioxetane3 1 3'-tricyclo[7.3. 1. 0$^{2,7}$]tridec-2,7-ene], disodium salt;

[(4-methoxy]-4-(3-phosphoryloxy-4-chlorophenyl)]spiro[1,2-dioxetane-3, 1 3'-tricyclo[7.3.1, 0$^{2,7}$]tridec-2,7-ene], disodium salt; and

[(4-methoxy)-4-(3-phosphoryloxyphenyl)]Spiro [1,2-dioxetane-3,9'-(2,4-diphenylbicyclo[3.3.1]non-2-ene)], disodium salt.

3. A method for generating light which comprises:
(a) providing a stable 1,2 dioxetane of the formulae:

(1)
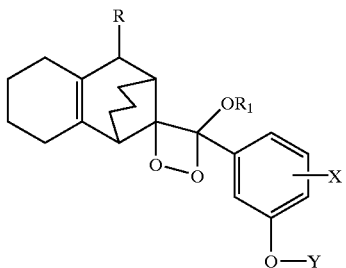

(2)
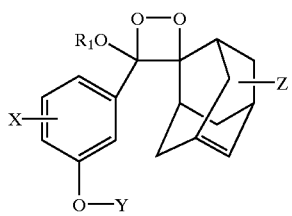

(3)
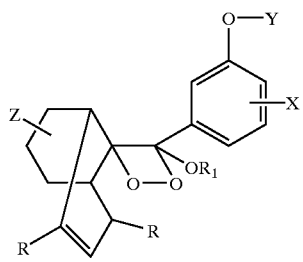

where $R_1$ is selected from the group consisting of alkyl, aryl, aralkyl, alkaryl, heteroalkyl, heteroaryl, cycloalkyl, cycloheteroalkyl, alkyletheralkyl, alkyletheraryl, alkyl(etheralkyl)2, alkyl(etheralkyl)3, alkyletherhaloalkyl, alkyl(etherhaloalkyl)2, alkylalkene, alkylalkyne, arylalkene, arylalkyne, halogenated alkyl(mono, di, tri or any position in normal or branched or cyclic chain), alkylalcohol, alkylnitrile, alkylamine, alkylacid (mono or dibasic) or the inorganic salts thereof, haloalkylalcohol, haloalkylnitrile, haloalkylamine, haloalkylacid (mono or dibasic) or inorganic salts, linker-flourescent molecule, linker-antibodies, linker-antigen, linker-biotin, linker-avidin, linker-protein or linker-carbohydrates or linker-lipids; Y is a hydrogen, alkyl, acetate, t-butyldimethylsilyl or an enzyme cleaveable group or an antibody cleaveable group; R is hydrogen, alkyl or substituted alkyl, aryl or substituted aryl, alkylaryl or substituted alkylaryl, arylalkyl or substituted arylalkyl; X is chloro-or hydrogen and Z is hydrogen, and (b) decomposing the stable 1,2-dioxetane with an activating agent to give the corresponding carbonyl group.

4. The method of claim 1 wherein the 1,2dioxtane is any one of the following:

[(4methoxy)-4-(3phosphoryloxyphenyl)]spiro [1,2-dioxetane-3,13'-(8-n-propyl)tricyclo[7.3.1.0$^{2,7}$)tridec-2,7-ene], disodium salt;

[(4-methoxy)-4-(3-phosphoryloxyphenyl)]Spiro [1,2-dioxetane-3,13'-tricyclo[7.3.1,0$^{2,7}$]tridec-2,7ene], disodium salt;

[(4methoxy)-4-(3-phosphoryloxyphenyl]spiro[1,2-dioxetane-3,2'-adamantan-4,5-ene], disodium salt;

[4(2,2,2-trifluoroethoxy)-4-phosphoryloxyphenyl)]spiro[1,2-dioxetane-3, 1 3'-tricyclo[7.3.1,0$^{2,7}$]tridec-2,7-ene], disodium salt;

[4-(2phenoxyethoxyl)-4-(3-phosphoryloxypheny)spiro[1,2-dioxetane3 1 3'-tricyclo[7.3.1.0$^{2,7}$]tridec-2,7-ene], disodium salt;

[(4-methoxy)-4-(3-phosphoryloxy-4-chlorophenyl)]spiro[1,2-dioxetane-3, 1 3'-tricyclo[7.3.1,0$^{2,7}$]tridec-2,7-ene], disodium salt; and

[(4-methoxy)-4-(3-phosphoryloxyphenyl)]Spiro[1,2-dioxetane-3,9'-(2,4diphenylbicyclo[3.3.1]non-2-ene)], disodium salt.

* * * * *